US012343388B2

(12) United States Patent
Ballard et al.

(10) Patent No.: US 12,343,388 B2
(45) Date of Patent: Jul. 1, 2025

(54) CLOSTRIDIOIDES DIFFICILE TcdB VARIANTS, VACCINES AND METHODS OF USE

(71) Applicant: The Board of Regents of the University of Oklahoma, Norman, OK (US)

(72) Inventors: Jimmy D. Ballard, Norman, OK (US); Sarah J. Bland, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 709 days.

(21) Appl. No.: 17/608,843

(22) PCT Filed: May 8, 2020

(86) PCT No.: PCT/US2020/032219
§ 371 (c)(1),
(2) Date: Nov. 4, 2021

(87) PCT Pub. No.: WO2020/231859
PCT Pub. Date: Nov. 19, 2020

(65) Prior Publication Data
US 2022/0313809 A1    Oct. 6, 2022

Related U.S. Application Data

(60) Provisional application No. 62/846,379, filed on May 10, 2019.

(51) Int. Cl.
| A61K 39/08 | (2006.01) |
| A61K 39/00 | (2006.01) |
| A61K 47/02 | (2006.01) |
| C12N 15/10 | (2006.01) |
| C12N 15/63 | (2006.01) |

(52) U.S. Cl.
CPC .............. *A61K 39/08* (2013.01); *A61K 47/02* (2013.01); *C12N 15/102* (2013.01); *C12N 15/63* (2013.01); *A61K 2039/52* (2013.01); *A61K 2039/55544* (2013.01)

(58) Field of Classification Search
None
See application file for complete search history.

(56) References Cited

U.S. PATENT DOCUMENTS

| 2008/0107373 | A1* | 5/2008 | Lee ......................... G02B 6/43 |
| | | | 257/E31.109 |
| 2012/0269841 | A1 | 10/2012 | Sidhu et al. |
| 2017/0008937 | A1* | 1/2017 | Melnyk .................. A61K 39/08 |
| 2017/0313749 | A1 | 11/2017 | Jansen et al. |
| 2018/0243365 | A1 | 8/2018 | Ballard et al. |

OTHER PUBLICATIONS

Zhang, Yongrong et. al.; "A Segment of 97 Amino Acids within the Translocation Domain of *Clostridium difficile* Toxin B is Essential for Toxicity"; PLOS One; vol. 8 Iss. 3; Mar. 2013; 8 pages.
Hunt, Jonathan J. et. al.; "Amino Acid Differences in the 1753-to-1851 Region of TcdB Influence Variations in TcdB1 and TcdB2 Cell Entry"; mSphere American Society for Microbiology; vol. 2 Iss. 4; Jul./Aug. 2017; 10 pages.
Larabee, Jason L. et. al.; "Cell-penetrating peptides derived from *Clostridium difficile* TcdB2 and a related large clostridial toxin"; Journal of Biological Chemistry; 293(5); 2018; pp. 1810-1819.
Chen, Shuyi et al.; "Identification of an Essential Region for Translocation of *Clostridium difficile* Toxin B"; Toxins; vol. 8 No. 8; Aug. 15, 2016; 13 pages.
Bland, Sarah J. et al.; "Deletion of a 19-Amino-Acid Region in *Clostridioides difficile* TcdB2 Results in Spontaneous Autoprocessing and Reduced Cell Binding and Provides a Nontoxic Immunogen for Vaccination"; Infection and Immunity; vol. 87 No. 8; Jul. 23, 2019; 14 pages.

* cited by examiner

Primary Examiner — Brian Gangle
(74) Attorney, Agent, or Firm — Winstead PC

(57) ABSTRACT

An immunogenic composition comprising a deletion mutant of a *Clostridioides difficile* TcdB toxin (such as TcdB2 or TcdB1) that lacks residues at least from amino acid residue 1769 to amino acid residue 1787 of a wild-type TcdB amino acid sequence or of a protein having high identity thereto, a vaccine comprising the immunogenic composition, a method of stimulating an immune response, a nucleic acid which encodes the amino acid sequence of the deletion mutant, a vector encoding the nucleic acid, and a host cell comprising the vector.

15 Claims, 11 Drawing Sheets
Specification includes a Sequence Listing.

TcdB2$_{\Delta 1769-1779}$:NVFKGNTISDK
TcdB2$_{\Delta 1769-1787}$:NVFKGNTISDKISFNFSDK       TcdB2$_{\Delta 2213-2223}$:YDMENESDKYY

| GTD | APD | TD | CTD |

TcdB2$_{\Delta 1751-1761}$:LMSTDEENKVS   TcdB2$_{\Delta 1847-1856}$:PPIKNLITGF
TcdB2$_{\Delta 1847-1866}$:PPIKNLITGFTTIGDDKYYF

CLOSTRIDIOIDES DIFFICILE TcdB VARIANTS, VACCINES AND METHODS OF USE

CROSS-REFERENCE TO RELATED APPLICATIONS

The present application claims priority under 35 U.S.C. § 119(e) to U.S. Ser. No. 62/846,379 filed May 10, 2019, the entirety of which is hereby expressly incorporated by reference herein.

STATEMENT REGARDING FEDERALLY SPONSORED RESEARCH OR DEVELOPMENT

This invention was made with government support under Grant Numbers R01AI119048 granted by the National Institutes of Health. The government has certain rights in the invention.

BACKGROUND

*Clostridioides difficile* (previously referred to as *Clostridium difficile*) toxin B (TcdB) is a 2366 amino acid intracellular bacterial toxin (e.g., see SEQ ID NO:1 and SEQ ID NO:3) that undergoes multiple conformational changes during cellular intoxication. The tertiary structure of TcdB includes four distinct domains which confer cell binding, cell entry, and enzymatic activities. The linear organization of TcdB's functional regions include a glucosyltransferase domain (GTD, amino acids 1-543), an autoprocessing domain (APD, amino acids 544-767), a multi-function translocation domain involved in cell interaction and membrane translocation (TD, amino acids 768-1852), and a carboxyl terminal domain (CTD, amino acids 1853-2366) containing combined repetitive oligopeptide (CROP) sequences. The cellular intoxication process is coordinated by stepwise conformational changes, and the timing and cellular location of these structural changes must be tightly regulated for TcdB to successfully intoxicate cells. Despite this characterization, the specific regions of TcdB which govern the conformational integrity prior to and during cellular intoxication are poorly defined.

The pH of the acidified endosome triggers the first known conformational change in TcdB, and results in exposure of hydrophobic regions and unfurling of four buried regions that form ion conducting channels. TcdB undergoes a second conformational change after binding inositol-hexakisphosphate (IP6) in the cell, which triggers the structural rearrangement that allows TcdB to adopt a conformer with an active APD. Following IP6 binding and APD activation, autoprocessing by the APD results in release of the GTD into the host cell cytosol where it inactivates small GTPases by glucosylation. The timing of both of these events is critical for TcdB intoxication of target cells. Indeed, one of the early descriptions of purified TcdB indicated the toxin was inactivated in extracellular acid pH conditions. In a similar manner, premature autoprocessing also inactivates TcdB. Thus, TcdB appears to maintain a soluble structure that allows receptor binding and cell entry, and coordinates acid pH-induced translocation and activation of the APD at the appropriate time and location during cellular intoxication.

One region of TcdB that appears to influence the conformation and stability of the protein spans amino acids 1753-1852, connecting the TD to the CROP containing CTD. The 1753-1852 region influences the exposure of carboxy-terminal epitopes in the CROP domain, and contributes to solution multimerization of carboxy-terminal fragments of the toxin. Peptides derived from the 1753-1852 region destabilize and inactivate TcdB through interactions with repeating sequences in the CROP domain. This stretch of 99 amino-acids also affects the overall activity of TcdB; sequence differences present in this region have been seen to influence the efficiency with which TcdB1 and TcdB2, the two major variants of the toxin, enter cells. As additional evidence supporting the importance of this region, it was found that deletion of residues 1756-1852 prevents TcdB1 from delivering the GTD into cells. Subsequent findings showed that residues 1756-1780 are necessary for membrane translocation of TcdB1. Taken altogether, these data support the idea that the 1753-1852 region of TcdB is important for cellular intoxication and likely plays an important role in maintaining the conformation of the toxin, while limiting exposure of neutralizing epitopes in the toxin.

The use of *C. difficile* toxin as a vaccine has been tried by others, but has had limited success. Therefore, there continues to be a need for a *C. difficile* vaccine that is both immunogenic and has low toxicity. It is to such a vaccine that the present disclosure is directed.

BRIEF DESCRIPTION OF THE DRAWINGS

FIG. 1 shows SDS-PAGE analysis and cytotoxicity of TcdB deletion mutants. (A) Domain layout of TcdB showing location of all internal deletions made and amino acid sequence of all deleted regions. (B) Coomassie stained SDS-PAGE (8%) showing each internal deletion mutant. (C) Cytotoxicity assay showing the cellular viability of CHO-K1 cells after 24 h treatment with TcdB2 and TcdB2 deletion mutants. Data are presented as mean±standard deviation of samples examined in triplicate, and are representative of three independent experiments.

DETAILED DESCRIPTION

Figure 2A:
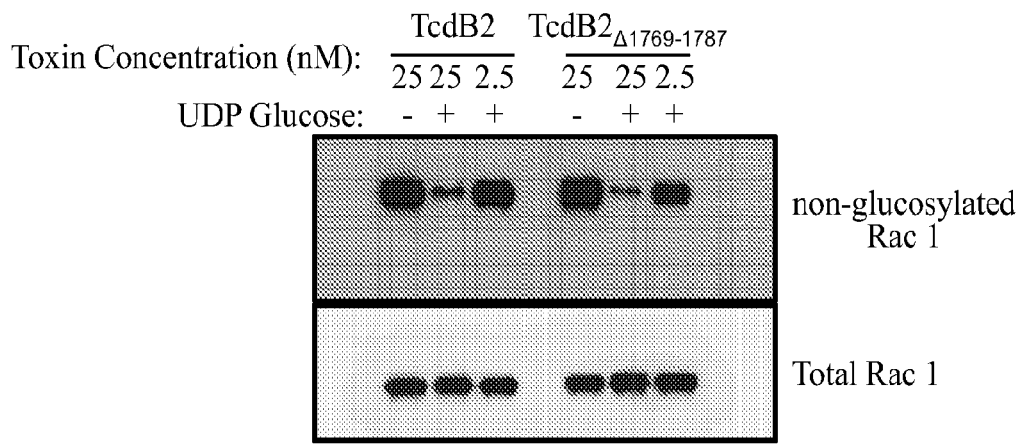
FIG. 2 shows results of an in vitro Rac1 glucosylation assay. (A) Immunoblot analysis of Rac1 glucosylation. TcdB2 and the TcdB2 variant with positions 1769-1787 deleted (TcdB2$_{\Delta1769-1787}$). Amounts of TcdB2$_{\Delta1769-1787}$ (25, 10, and 2.5 nM) were incubated separately with either purified Rac1 and UDP-glucose, or purified Rac1 alone. Blots are probed using an antibody specific for non-glucosylated Rac1 and an antibody recognizing total Rac1. A loss of signal is seen upon glucosylation of Rac1 when assessing the blot with the antibody against non-glucosylated Rac1. (B) Densitometry analysis of three independent glucosylation experiment immunoblots. Results are presented as mean±standard deviation, with significance determined by one-way ANOVA on ranks.

In the present disclosure, the 1753-1852 amino acid sequence of TcdB2 was investigated to identify sequences that influence the cytotoxicity of TcdB, while preserving neutralizing epitopes in the protein. In one non-limiting embodiment, it was found that a variant in which the amino acids in positions 1769-1787 of TcdB2 were deleted (TcdB2$_{\Delta1769-1787}$) leads to pre-mature autoprocessing and prevents interaction with multiple cell types, while maintaining both immunogenicity and neutralizing epitopes of the wild type protein. In at least certain embodiments, the present disclosure is directed to a deletion mutant of a *Clostridioides difficile* TcdB toxin, having a deletion of 19 amino acids corresponding to amino acids 1769 to 1787 of the TcdB toxin. For example, the TcdB toxin may have amino acid sequence SEQ ID NO:1 or SEQ ID NO:3, or may have an amino acid sequence having at least 90% identity to SEQ ID NO:1 or SEQ ID NO:3. The deletion mutant may be used to form a vaccine against *Clostridioides difficile*. The vaccine may be used as a treatment against a *Clostridioides difficile* infection in a patient or as a prophylactic treatment to inhibit such an infection in, for example, a person who is in a population with an enhanced risk to such infection.

In certain embodiments, the present disclosure is directed to vaccine compositions for initiating an immune response against *Clostridioides difficile*. In non-limiting embodiments, the vaccine may comprise a deletion mutant of TcdB1 and/or TcdB2, wherein the deletion comprises the 19 amino acid sequence from amino acid position 1769 through amino acid position 1787 (SEQ ID NO:2 for toxin TcdB2 (a protein having the amino acid sequence SEQ ID NO:1), and SEQ ID NO:4 for toxin TcdB1 (a protein having the amino acid sequence SEQ ID NO:3). The deletion mutant may further comprise at least one deletion and/or substitution (as defined elsewhere herein) within amino acids 1 to 1752, amino acids 1753-1768, amino acids 1788-1852, and/or within 1853 to 2366 of the wild-type TcdB1 or TcdB2 amino acid sequence, respectively, wherein the deletion mutant is at least 90% identical to the wild-type TcdB1 or TcdB2 amino acid sequence (SEQ ID NO:3 and SEQ ID NO:1, respectively). The immunogenic composition may further comprise a pharmaceutically acceptable carrier and/or an adjuvant. In certain embodiments, the toxin is obtained from one of *C. difficile* strains BI17, NAP1, B1, 027, R20291, and VPI 10463.

Before further detailed description of various embodiments of the compositions and methods of use thereof of the present disclosure, it is to be understood that the present disclosure is not limited in application to the details of methods and compositions as set forth in the following description. The description provided herein is intended for purposes of illustration only and is not intended to be construed in a limiting sense. The present disclosure is capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that various embodiments of the present disclosure may be practiced without these specific details. In other instances, features which are well known to persons of ordinary skill in the art have not been described in detail to avoid unnecessary complication of the description. It is intended that all alternatives, substitutions, modifications and equivalents apparent to those having ordinary skill in the art are included within the scope of the present disclosure as defined herein. Thus the examples described below, which include particular embodiments, will serve to illustrate the practice of the present disclosure, it being understood that the particulars shown are by way of example and for purposes of illustrative discussion of particular embodiments only and are presented in the cause of providing what is believed to be a useful and readily understood description of procedures as well as of the principles and conceptual aspects of the inventive concepts. Thus, while the compositions and methods of the present disclosure have been described in terms of particular embodiments, it will be apparent to those of skill in the art that variations may be applied to the compositions and/or methods and in the steps or in the sequence of steps of the method described herein without departing from the concept, spirit, and scope of the inventive concepts disclosed herein.

All patents, published patent applications, and non-patent publications mentioned in the specification are indicative of the level of skill of those skilled in the art to which the present disclosure pertains. Each patent, published patent application, and non-patent publication referenced in any portion of this application is expressly incorporated herein by reference in its entirety to the same extent as if the individual patent, or published patent application, or non-patent publication was specifically and individually indicated to be incorporated by reference.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example.

Throughout this application, the terms "about" and "approximately" are used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, observer error, and combinations thereof, for example. The term "about" or "approximately", where used herein when referring to a measurable value such as an amount, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 80% of the time, at least 90% of the time, at least 91% of the time, at least 92% of the time, at least 93% of the time, at least 94% of the time, at least 95% of the time, at least 96% of the time, at least 97% of the time, at least 98% of the time, or at least 99% of the time.

As used herein any reference to "one embodiment" or "an embodiment" means that a particular element, feature, composition, structure, or characteristic described in connection with the embodiment is included in at least one embodiment. The appearances of the phrase "in one embodiment" in various places in the specification are not necessarily all referring to the same embodiment.

The terms "mutant" and "variant" are intended to refer to a protein, peptide, nucleic acid or organism which has at least one amino acid or nucleotide which is different from the wild type version of the protein, peptide, nucleic acid, or organism and includes, but is not limited to, point substitutions, multiple contiguous or non-contiguous substitutions, deletions, chimeras, or fusion proteins, and the nucleic acids which encode them. Examples of conservative amino acid substitutions include, but are not limited to, substitutions made within the same group such as within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, and valine), aromatic amino acids (such as phenylalanine, tryptophan, tyrosine) and small amino acids (such as glycine, alanine, serine, threonine, methionine). Other examples of possible substitutions are described below. A deletion refers to a removal of one or more amino acids from a wild-type amino acid sequence, for example.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism without reference to how the active agent has its physiological effects.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species (e.g., the peptide compound) is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

The terms "subject" and "patient" are used interchangeably herein and will be understood to refer to a warm blooded animal, particularly a mammal. Non-limiting examples of mammals within the scope and meaning of this term include dogs, cats, rabbits, rats, mice, guinea pigs, chinchillas, hamsters, ferrets, horses, pigs, goats, cattle, sheep, zoo animals, camels, llamas, non-human primates, including Old and New World monkeys and non-human primates (e.g., cynomolgus macaques, chimpanzees, rhesus monkeys, orangutans, and baboons), and humans.

"Treatment" refers to therapeutic treatments. "Prevention" refers to prophylactic or preventative treatment measures. The term "treating" refers to administering the composition to a patient for therapeutic purposes.

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of an active agent which is sufficient to exhibit a detectable therapeutic effect without excessive adverse side effects (such as toxicity, irritation and allergic response) commensurate with a reasonable benefit/risk ratio when used in the manner of the present disclosure. The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "ameliorate" means a detectable or measurable improvement in a subject's condition, disease or symptom thereof. A detectable or measurable improvement includes a subjective or objective decrease, reduction, inhibition, suppression, limit or control in the occurrence, frequency, severity, progression, or duration of the condition or disease, or an improvement in a symptom or an underlying cause or a consequence of the disease, or a reversal of the disease. A successful treatment outcome can lead to a "therapeutic effect," or "benefit" of ameliorating, decreasing, reducing, inhibiting, suppressing, limiting, controlling or preventing the occurrence, frequency, severity, progression, or duration of a disease or condition, or consequences of the disease or condition in a subject.

A decrease or reduction in worsening, such as stabilizing the condition or disease, is also a successful treatment outcome. A therapeutic benefit therefore need not be complete ablation or reversal of the disease or condition, or any one, most or all adverse symptoms, complications, consequences or underlying causes associated with the disease or condition. Thus, a satisfactory endpoint may be achieved when there is an incremental improvement such as a partial decrease, reduction, inhibition, suppression, limit, control, or prevention in the occurrence, frequency, severity, progression, or duration, or inhibition or reversal of the condition or disease (e.g., stabilizing), over a short or long duration of time (hours, days, weeks, months, etc.). Effectiveness of a method or use, such as a treatment that provides a potential therapeutic benefit or improvement of a condition or disease, can be ascertained by various methods and testing assays.

Where used herein, the term "eliciting an immune response" or "inducing an immune response" means initiating, triggering, causing, enhancing, improving or augmenting any response of the immune system, for example, of either a humoral or cell-mediated nature. The initiation or enhancement of an immune response can be assessed using assays known to those skilled in the art including, but not limited to, antibody assays (for example ELISA assays), antigen specific cytotoxicity assays and the production of cytokines (for example ELISPOT assays).

Where used herein, the term "*Clostridioides difficile*" includes all strains of *C. difficile*, including, but not limited to, ribotype 027 (a.k.a. NAP1 and BI), VP110463 strain (ribotype 003), ribotype W (a.k.a. NAP2), MOH 900 and MOH 718.

Where used herein, the term "vaccine" refers to an immunogenic (antigenic) composition that induces an immune response in a subject to prevent or reduce the severity of a *C. difficile* infection, treat a *C. difficile* infection, and/or reduce shedding of *C. difficile* in a subject.

The immunogenic compositions described herein may be substantially pure, or combined with one or more immune-stimulating adjuvants. The vaccine may comprise or be administered with an adjuvant. The term "adjuvant" refers to a compound that, when used in combination with a specific immunogen in a formulation, will augment or otherwise alter or modify the resultant immune response. In certain embodiments, the immunogenic compositions comprise an alum (aluminum salt) adjuvant. Examples of alum-type adjuvants, which are usually provided as a hydrated gel, include but are not limited to, aluminum hydroxide (e.g. Alhydrogel®), aluminum phosphate (e.g., Adju-Phos®) aluminum hydroxyphosphate, aluminum sulfate, aluminum potassium sulfate, aluminum sodium sulfate, and aluminum ammonium sulfate. Other examples of adjuvants which may be used include, but are not limited to, Freund's incomplete adjuvant, Freund's Complete adjuvant, alum, monophosphoryl lipid A, alum phosphate or hydroxide, QS-21, salts, i.e., $AlK(SO_4)_2$, $AlNa(SO_4)_2$, $AlNH_4(SO_4)_2$, silica, kaolin, muramyl dipeptide, carbon polynucleotides, i.e., poly IC and poly AU, and QuilA and Alhydrogel and the like, 1018 ISS, Ribi, Amplivax, AS15, BCG, CP-870,893, CpG7909, CyaA, Mologen's dSLIM, GM-CSF, IC30, IC31, Imiquimod, ImuFact IMP321, interferon-alpha or beta, IS Patch, ISS, ISCOMs, Juvlmmune, LipoVac, MF59, and other non-toxic LPS derivatives, Montanide IMS 1312, Montanide ISA 206, Montanide ISA 50\1, Montanide ISA-51, OK-432, OM-174, nontoxic lipid A-related adjuvants such as, but not limited to, nontoxic monophosphoryllipid A (see, e.g., Persing et al., Trends Microbial. 10:s32-s37 (2002)), for example, 3 De-0-acylated monophosphoryllipid A (MPL) (see, e.g., United Kingdom Patent Application No. GB 2220211), silica, kaolin, muramyl dipeptide (MDP), lipopolysaccharide (LPS), carbon polynucleotides, i.e., poly IC and poly AU, QS21 and QuilA that comprise a triterpene glycoside or saponin isolated from the bark of the *Quillaja saponaria* Molina tree found in South America (see, e.g., Kensil et al., in Vaccine Design: The Subunit and Adjuvant Approach (eds. Powell and Newman, Plenum Press, N Y, 1995); U.S. Pat. No. 5,057,540), polymeric or monomeric amino acids such as polyglutamic acid or polylysine, liposomes, and CpG (see, e.g., Klinman, Int. Rev. Immunol. 25(3-4):135-54 (2006); and U.S. Pat. No. 7,402,572. Other examples of adjuvants that may be used in the compositions disclosed herein include but are not limited to those disclosed in U.S. Pat. No. 8,895,514. Optionally, immunogenic composition can be combined with or administered with immunomodulators and immunostimulants. The vaccine may comprise microparticles such as liposomes or immune-stimulating complexes (ISCOMs).

In certain embodiments, as noted, the adjuvant may comprise aluminum hydroxide or aluminum phosphate, or an aluminum-free adjuvant. In certain embodiments, the immunogenic composition is formulated with an adjuvant comprising an immunologically active saponin fraction presented in the form of a liposome. The adjuvant may further comprise a lipopolysaccharide. The adjuvant may include a saponin, such as QS21. For example, in one embodiment, the adjuvant contains QS21 in a liposomal formulation. In one embodiment, the adjuvant system includes 3-Deacylated monophoshoryl lipid A (3D-MPL) and QS21. For example, in one embodiment, the adjuvant contains 3D-MPL and QS21 in a liposomal formulation. Optionally, the adjuvant system also contains cholesterol. In one specific embodiment, the adjuvant includes QS21 and cholesterol. Optionally, the adjuvant system contains 1, 2-Dioleoyl-sn-Glycero-3-phosphocholine (DOPC). For example, in one specific adjuvant system contains cholesterol, DOPC, 3D-MPL and QS21.

The immunogenic composition may include an adjuvant formulated in a dose that includes: from about 0.1 to about 0.5 mg cholesterol; from about 0.25 to about 2 mg DOPC; from about 10 μg to about 100 μg 3D-MPL; and from about 10 μg to about 100 μg QS21. In other embodiments, the immunogenic composition is formulated with a fractional dose (that is a dose, which is a fraction of the preceding single dose formulations, such as one half of the preceding quantity of components (cholesterol, DOPC, 3D-MPL and QS21), ¼ of the preceding quantity of components, or another fractional dose (e.g., ⅓, ⅙, etc.) of the preceding quantity of components. In one embodiment, the immunogenic composition includes an adjuvant containing combinations of lipopolysaccharide and *Quillaja* saponins that have been disclosed previously, for example in EP0671948. The adjuvant may further comprise immunostimulatory oligonucleotides (for example, CpG) or a carrier.

A suitable saponin for use is Quil A and its derivatives. As noted, Quil A is a saponin preparation isolated from the South American tree *Quillaja saponaria* Molina and was first described by Dalsgaard et al. in 1974 ("Saponin adjuvants", Archiv. fur die gesamte Virusforschung, Vol. 44, Springer Verlag, Berlin, p 243-254) to have adjuvant activity. Purified fragments of Quil A have been isolated by HPLC which retain adjuvant activity without the toxicity associated with Quil A (EP 0 362 278), for example QS7 and QS21 (also known as QA7 and QA21). QS21 is a natural saponin derived from the bark of *Quillaja saponaria*

Molina, which induces CD8+ cytotoxic T cells (CTLs), Th1 cells and a predominant IgG2a antibody response.

When the adjuvant comprises an immunologically active saponin fraction presented in the form of a liposome, the adjuvant may further comprise a sterol. Suitably the sterol may be provided at a ratio of saponin:sterol of from 1:1 to 1:100 w/w, such as from 1:1 to 1:10 w/w; or 1:1 to 1:5 w/w. In a specific embodiment, QS21 is provided in its less reactogenic composition where it is quenched with an exogenous sterol, such as cholesterol for example. Several particular forms of less reactogenic compositions wherein QS21 is quenched with an exogenous cholesterol exist. In a specific embodiment, the saponin/sterol is in the form of a liposome structure (WO 96/33739, Example 1). In this embodiment the liposomes suitably contain a neutral lipid, for example phosphatidylcholine, which is suitably non-crystalline at room temperature, for example eggyolk phosphatidylcholine, DOPC or dilauryl phosphatidylcholine. The liposomes may also contain a charged lipid which increases the stability of the lipsome-QS21 structure for liposomes composed of saturated lipids. In these cases the amount of charged lipid is suitably 1-20% w/w, preferably 5-10%. The ratio of sterol to phospholipid is 1-50% (mol/mol), suitably 20-25%. Suitable sterols include β-sitosterol, stigmasterol, ergosterol, ergocalciferol and cholesterol. In one particular embodiment, the adjuvant composition comprises cholesterol as sterol.

Where the active saponin fraction is QS21, the ratio of QS21: sterol may be in the order of 1:100 to 1:1 (w/w), between 1:10 to 1:1 (w/w), or 1:5 to 1:1 (w/w). Suitably excess sterol is present, the ratio of QS21:sterol being at least 1:2 (w/w). In one embodiment, the ratio of QS21:sterol is 1:5 (w/w). The sterol is suitably cholesterol. In one embodiment, the immunogenic composition comprises an immunologically active saponin, such as QS21, at a level of about 1-about 100 µg per dose, for example at an amount of about 50 µg. In one embodiment, the invention provides a dose of an immunogenic composition comprising immunologically active saponin, preferably QS21, at a level of 75 µg or less, for example between 1 µg and 60 µg. In one embodiment, the dose of the immunogenic composition comprises QS21 at a level of approximately around 50 µg, for example between 45 µg and 55 µg. In another embodiment the dose of the immunogenic composition comprises QS21 at a level of around 25 µg for example between 10-40 µg. For example, a 0.5 ml vaccine dose volume may contain 10 µg to 50 µg of QS21.

In compositions comprising a lipopolysaccharide, the lipopolysaccharide may be present at, but is not limited to, an amount of about 1 to about 100 µg per dose, for example at an amount of about 50 µg. The lipopolysaccharide may be a non-toxic derivative of lipid A, particularly monophosphoryl lipid A or more particularly 3-Deacylated monophoshoryl lipid A (3D-MPL). 3D-MPL is sold under the name MPL by GlaxoSmithKline Biologicals S.A. and is referred throughout the document as MPL or 3D-MPL. See, for example, U.S. Pat. Nos. 4,436,727; 4,877,611; 4,866,034 and 4,912,094. 3D-MPL primarily promotes CD4+ T cell responses with an IFN-γ (Th1) phenotype. 3D-MPL can be produced according to the methods disclosed in GB 2 220 211 A. Chemically it is a mixture of 3-deacylated monophosphoryl lipid A with 3, 4, 5 or 6 acylated chains. Preferably in the compositions of the present invention small particle 3D-MPL is used. Small particle 3D-MPL has a particle size such that it may be sterile-filtered through a 0.22 µm filter. Such preparations are described in WO 94/21292. For example, a dose of an immunogenic composition herein may contain a lipopolysaccharide, preferably 3D-MPL, at a level of 75 µg or less, for example between 1 µg and 60 µg. For example, a 0.5 ml vaccine dose volume may contain 25 µg or 50 µg of 3D-MPL per dose.

In certain embodiments, the volume of the dose is 0.5 ml. In a further embodiment, the immunogenic composition is in a volume suitable for a dose which volume is higher than 0.5 ml, for example 0.6, 0.7, 0.8, 0.9 or 1 ml. In a further embodiment, the human dose is between 1 ml and 1.5 ml. In particular embodiments, the dose of the immunogenic composition disclosed herein refers to human dose. By the term "human dose" is meant a dose which is in a volume suitable for human use. Generally this is between 0.3 and 1.5 ml. In one embodiment, a human dose is 0.5 ml. In a further embodiment, a human dose is higher than 0.5 ml, for example 0.6, 0.7, 0.8, 0.9 or 1 ml. In a further embodiment, a human dose is between 1 ml and 1.5 ml.

In certain embodiments, a saponin and a lipopolysaccharide, such as QS21 and 3D-MPL, respectively, are present in the same final concentration (1:1) per dose of the immunogenic composition i.e. the ratio of QS21:3D-MPL is 1:1. In one aspect of this embodiment, a dose of immunogenic composition comprises a final level of 25 µg of 3D-MPL and 25 µg of QS21 or 50 µg of 3D-MPL and 50 µg of QS21.

In certain embodiments, the adjuvant includes an oil-in-water emulsion. In one embodiment the adjuvant comprises an oil in water emulsion, wherein the oil in water emulsion comprises a metabolizable oil, a tocol, and an emulsifier. For example, the oil-in-water emulsion can include an oil phase that incorporates a metabolizable oil, and an additional oil phase component, such as a tocol. The oil-in-water emulsion may also contain an aqueous component, such as a buffered saline solution (e.g., phosphate buffered saline). In addition, the oil-in-water emulsion typically contains an emulsifier. In one embodiment, the metabolizable oil is squalene. In one embodiment, the tocol is alpha-tocopherol. In one embodiment, the emulsifier is a nonionic surfactant emulsifier (such as polyoxyethethylene sorbitan monooleate, Polysorbate 80™, TWEEN80™). In exemplary embodiments, the oil-in-water emulsion contains squalene and alpha tocopherol in a ratio which is equal or less than 1 (w/w). The metabolizable oil in the oil-in-water emulsion may be present in an amount of 0.5-10 mg, for example. The tocol in the oil-in-water emulsion may be present in an amount of 0.5-11 mg for example. The emulsifying agent may be present in an amount of 0.4-4 mg, for example. The meaning of the term metabolizable is well known in the art. The oil may be any vegetable oil, fish oil, animal oil or synthetic oil, which is not toxic to the recipient and is capable of being transformed by metabolism. Nuts, seeds, and grains are common sources of vegetable oils. Synthetic oils may also be used, such as commercially available oils such as caprylic/capric triglycerides made using glycerol from vegetable oil sources and medium-chain fatty acids (MCTs) from coconut or palm kernel oils) and others. A particularly suitable metabolizable oil is squalene. Squalene (2,6,10,15,19,23-Hexamethyl-2,6,10,14,18,22-tetracosahexaene) is an unsaturated oil which is found in large quantities in shark-liver oil, and in lower quantities in olive oil, wheat germ oil, rice bran oil, and yeast. In non-limiting embodiments, the metabolizable oil may be present in the adjuvant composition in an amount of 0.5-10 mg, e.g., 1-10, 2-10, 3-9, 4-8, 5-7, or 5-6 mg (e.g., 2-3, 5-6, or 9-10 mg) per dose.

Tocols are well known in the art. Exemplary embodiments are described in EP0382271. The tocol may be alpha-tocopherol or a derivative thereof such as alpha-tocopherol succinate (also known as vitamin E succinate). Said tocol may be present in in an amount of 0.5-20 mg, for example, such as an amount in a range of 1-15, 2-10, 3-9, 4-8, 5-7, or 5-6 mg per dose.

The oil in water emulsion may further comprise an emulsifying agent. The emulsifying agent may be, for example, polyoxyethylene sorbitan monooleate. In a particular embodiment the emulsifying agent may be Polysorbate 80™ (Polyoxyethylene (20) sorbitan monooleate) or Tween 80™. Said emulsifying agent may be present in the adjuvant composition in an amount of 0.1 mg to 10 mg, for example, such as an amount in a range of 0.1-5, 0.2-5, 0.3-4, 0.4-3 or 2-3 mg.

Where the adjuvant is in a liquid form and is to be combined with a liquid form of a polypeptide composition, the adjuvant composition in a human dose will generally be a fraction of the intended final volume of the human dose, for example approximately half of the intended final volume of the human dose, for example a 350 µl volume for an intended human dose of 0.7 ml, or a 250 µl volume for an intended human dose of 0.5 ml. The adjuvant composition is diluted when combined with the polypeptide antigen composition to provide the final human dose of vaccine. The final volume of such dose will of course vary dependent on the initial volume of the adjuvant composition and the volume of polypeptide antigen composition added to the adjuvant composition. In an alternative embodiment, a liquid adjuvant is used to reconstitute a lyophilized polypeptide composition. In this embodiment, the human dose of the adjuvant composition is approximately equal to the final volume of the human dose. The liquid adjuvant composition is added to the vial containing the lyophilized polypeptide composition. The final human dose can vary between 0.5 and 1.5 ml, for example. In an oil in water emulsion, the oil and emulsifier should be in an aqueous carrier. The aqueous carrier may be, for example, phosphate buffered saline. The oil-in-water emulsion systems of the present disclosure generally have a small oil droplet size in the sub-micron range. Suitably the droplet sizes will be in the range 120 to 750 nm, such as in the range of 120 to 600 nm in diameter, or the range of 120 to 300 nm in diameter.

In certain embodiments the immunogenic composition further comprises additional antigens, such as antigens derived from a bacterium selected from the group S. pneumoniae, H. influenzae, N. meningitidis, E. coli, M catarrhalis, Clostridium tetani (tetanus), Corynebacterium diphtheria (diphtheria), Bordetella pertussis (pertussis), S. epidermidis, enterococci, S. aureus, and Pseudomonas aeruginosa. In a further embodiment the immunogenic composition of the invention may comprise further antigens from C. difficile. Optionally the immunogenic composition further comprises a saccharide from C. difficile.

The vaccine preparations containing immunogenic compositions of the present disclosure may be used to protect a mammal susceptible to C. difficile infection or treat a mammal with a C. difficile infection, by means of administering said vaccine via systemic or mucosal route or other suitable route. These administrations may include injection via the intramuscular, intraperitoneal, intradermal or subcutaneous routes; or via mucosal administration to the oral/alimentary, respiratory, genitourinary tracts. Although the vaccine may be administered as a single dose, components thereof may also be co-administered together at the same time or at different times (for instance pneumococcal saccharide conjugates could be administered separately, at the same time or 1-2 weeks after the administration of the any bacterial protein component of the vaccine for coordination of the immune responses with respect to each other). In addition to a single route of administration, two different routes of administration may be used. For example, saccharides or saccharide conjugates may be administered intramuscularly (IM) or intradermally (ID) and bacterial proteins may be administered intranasally (IN) or intradermally (ID). In addition, the vaccines may be administered IM for priming doses and IN for booster doses.

In certain non-limiting embodiments, the content of mutant toxins in the vaccine will typically be in the range 1-250 µg, 5-100 µg, or in the range 5-25 µg. Following an initial vaccination, subjects may receive one or several booster immunizations adequately spaced. Vaccine preparation is generally described in Vaccine Design ("The subunit and adjuvant approach" (eds Powell M. F. & Newman M. J.) (1995) Plenum Press New York). A non-limiting description of encapsulation of the immunogenic composition and/or vaccine formulation within liposomes is described by Fullerton, U.S. Pat. No. 4,235,877.

In one aspect, the present disclosure includes a vaccine kit, comprising a vial containing an immunogenic composition of the disclosure, optionally in lyophilized form, and further comprising a vial containing an adjuvant as described herein. It is envisioned that in this aspect, the adjuvant will be used to reconstitute the lyophilized immunogenic composition.

In a further, the disclosure includes a method of preventing or treating a subject for a C. difficile infection, comprising administering to the subject an immunoprotective dose of the immunogenic composition or vaccine or kit of the invention. In one embodiment there is provided a method of treating primary and/or recurrence episodes of C. difficile infection comprising administering to the subject an immunoprotective dose of the immunogenic composition or vaccine or kit of the present disclosure. In one embodiment there is provided a prophylactic method of treating a subject to prevent or inhibit a C. difficile infection in the subject (for example a person having an enhanced risk of acquiring said infection) comprising administering to the subject an immunoprotective dose of the immunogenic composition or vaccine or kit of the present disclosure. For prophylactic treatment against C. difficile infection, the immunogenic composition or the antibody produced therefrom can be administered prior to exposure of a subject to the bacteria so that the resulting immune response can inhibit or reduce the severity of the bacterial infection.

Generation of a protective immune response by the vaccine can be measured by the development of antibodies. The amounts of the toxin mutant described herein that can form a protective immune response typically are in a unit dosage form of about 0.001 µg to 100 mg per kg of body weight, more preferably 0.01 µg to 1 mg/kg of body weight, and more preferably about 0.1 µg to about 10 µg/kg body weight, for example, at an interval of about 1 to 6 weeks intervals between immunizations.

The vaccine compositions are administered to animals which may become infected by the disease organism described herein, including but not limited to dogs, cats, rabbits, rodents, horses, livestock (e.g., cattle, sheep, goats, and pigs), zoo animals, ungulates, monkeys, primates, and humans.

The vaccine compositions may be made from an antigenic fragment of a mutant TcdB toxin described herein, wherein such fragment is large enough to stimulate a protective immune response, including but not limited to a cross-neutralizing response. For example, the fragment may comprise a minimum length of 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, or 2350 or more amino acids of the mutant TcdB1 and/or TcdB2 toxin.

The vaccines described herein are also useful to generate neutralizing antibodies which can be used as a passive immune serum to treat or ameliorate the symptoms in patients. A vaccine composition as described above could be administered to an organism or animal such as a horse or other suitable mammal, wherein a neutralizing antibody response is generated. These neutralizing antibodies can then be harvested, purified, and utilized to treat patients exhibiting symptoms. The neutralizing antibodies are administered to patients exhibiting disease symptoms in an amount effective to neutralize the effect of the pathogen. The neutralizing antibodies can be administered intravenously, intramuscularly, intradermally, subcutaneously, and the like. In one embodiment of the treatment method, the neutralizing antibody can be administered in conjunction with antibiotic therapy. The amount of neutralizing antibodies typically administered is about 1 mg of antibody to 1000 mg/kg, more preferably about 50-200 mg/kg of body weight.

The immunogenic composition may be administered for example, only once, or at an interval of about 1 week to 6 weeks between immunizations. An immunogenic composition (i.e., vaccine) is administered in an amount sufficient to elicit production of antibodies as part of an immunogenic response. In certain embodiments, the immunogenic composition can be administered repeatedly with one to three month intervals between each dose and with an optional booster dose later in time. For example, after the first injection, a subject may receive one or more booster immunizations according to a particular (but non-limiting) schedule that may vary according to, inter alia, the immunogenic composition, adjuvants (if any) and/or the particular subject. Booster immunizations may be administered multiple times (e.g., two times or three times or four times or more), at desired time intervals ranging from, for example, about 2 weeks to about 26 weeks, such as 2, 4, 8, 12, 16, or 26 week intervals. The time intervals between different doses (e.g., between the primary dose and second dose, or between the second dose and a third dose) may not be the same, and the time interval between each two doses may be determined independently.

The immunogenic composition or the antibody produced therefrom can be administered post-infection or after a presumed infection, exposure or manifestation of clinical symptoms. For example, immunogenic composition or the antibody can be administered as a single dose or in multiple sequential doses, in a time period up to 8 hours post infection, 24 hours post infection, 48 hours post infection, 72 hours post infection, 4 days post infection, 5 days post infection, 6 days post infection, 7 days post infection, 10 days post infection, 2 weeks post infection, 3 weeks post infection, 4 weeks post infection, a month post infection, 2 months post infection, or later, post infection.

As noted, vaccines and/or immunogenic formulations of the present disclosure may be administered on a dosage schedule, for example, an initial administration of the vaccine composition with subsequent booster administrations. In particular embodiments, a second dose of the composition is administered anywhere from two weeks to one year, for example from about 1, or about 2, or about 3, or about 4, or about 5, to about 6 months, after the initial administration. Additionally, a third dose may be administered after the second dose and from about three months to about two years, or even longer, such as about 4, or about 5, or about 6 months, or about 7 months to about one year after the initial administration. The third dose may be optionally administered when no or low levels of specific immunoglobulins are detected in the serum and/or urine or mucosal secretions of the subject after the second dose. In a non-limiting embodiment, a second dose is administered about one month after the first administration and a third dose is administered about six months after the first administration. In another embodiment, the second dose is administered about six months after the first administration. In another embodiment, the compositions can be administered as part of a combination therapy. For example, the compositions of the present disclosure can be formulated with other immunogenic compositions, antivirals, or antibiotics.

The vaccine composition may be prepared as a pharmaceutical composition containing an immunoprotective, non-toxic deletion mutant in a non-toxic and sterile pharmaceutically acceptable carrier. The vaccines of the present disclosure can be administered to the appropriate subject in any manner known in the art, e.g., orally intramuscularly, intravenously, sublingual mucosal, intraarterially, intrathecally, intradermally, intraperitoneally, intranasally, intrapulmonarily, intraocularly, intravaginally, intrarectally or subcutaneously. They can be introduced into the gastrointestinal tract or the respiratory tract, e.g., by inhalation of a solution or powder containing the conjugates. In some embodiments, the compositions can be administered via absorption via a skin patch. Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained.

A vaccine composition is administered as an "effective dose", i.e. an amount of the immunogenic composition sufficient to elicit production of antibodies as part of an immunogenic response. Dosage for any given patient depends upon many factors, including the patient's size, general health, sex, body surface area, age, the particular compound to be administered, time and route of administration, and other drugs being administered concurrently. Determination of optimal dosage is well within the abilities of a pharmacologist of ordinary skill. If necessary the vaccine will be administered repeatedly with one to three month intervals between each dose and with an optional booster dose later in time. Actual methods of preparing the appropriate dosage forms are known, or will be apparent, to those skilled in this art; for example, see Remington's Pharmaceutical Sciences, latest edition.

As used herein an "effective dose" generally refers to that amount of the presently disclosed deletion mutant provided in a composition with ancillary compounds such as delivery vehicles and/or adjuvants that is sufficient to induce immunity, to prevent and/or ameliorate an infection or to reduce at least one symptom of an infection or disease, to delay or minimize the onset of an infection or disease, provide a therapeutic benefit in the treatment or management of an infection or disease, and/or to enhance the efficacy of another immunogen. provides a therapeutic benefit in the treatment or management of an infection or disease. An effective dose may also be the amount sufficient to enhance a subject's (e.g., a human's) own immune response against a subsequent exposure to an infectious agent or disease. Levels of immunity can be monitored, e.g., by measuring amounts of neutralizing secretory and/or serum antibodies, e.g., by plaque neutralization, complement fixation, enzymelinked immunosorbent, or microneutralization assay, or by measuring cellular responses, such as, but not limited to cytotoxic T cells, antigen presenting cells, helper T cells, dendritic cells and/or other cellular responses. T cell responses can be monitored, e.g., by measuring, for example, the amount of CD4$^+$ and CD8$^+$ cells present using specific markers by fluorescent flow cytometry or T cell assays, such as but not limited to T-cell proliferation assay, T-cell cytotoxic assay, TETRAMER assay, and/or ELISPOT assay. In the case of a vaccine, an "effective dose" is one that prevents disease and/or reduces the severity of symptoms. As used herein, the terms "immunogens" or "antigens" refer to substances such as proteins, peptides, nucleic acids that are capable of eliciting an immune response. Both terms also encompass epitopes, and are used interchangeably.

As used herein the term "immune stimulator" refers to a compound that enhances an immune response via the body's own chemical messengers (cytokines). These molecules comprise various cytokines, lymphokines and chemokines with immunostimulatory, immunopotentiating, and pro-inflammatory activities, such as interferons (IFN-gamma), interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immune stimulator molecules can be administered in the same formulation as the immunogenic compositions, or can be administered separately. Either the protein or an expression vector encoding the protein can be administered to produce an immunostimulatory effect.

In other embodiments, the present disclosure includes a kit comprising (a) a container that contains one or more pharmaceutical compositions as described herein, in solution or in lyophilized form; (b) optionally, a second container containing a diluent or reconstituting solution for the lyophilized formulation; and (c) optionally, instructions for (i) use of the solution or (ii) reconstitution and/or use of the lyophilized formulation. The kit optionally further comprises one or more of (iii) a buffer, (iv) a diluent, (v) a filter, (vi) a needle, or (v) a syringe. The container is (in a particular, non-limiting embodiment) a bottle, a vial, a syringe or test tube; and it may be a multi-use container. The container may be formed from a variety of materials such as glass or plastic. The kit and/or container may contain instructions on or associated with the container that indicates directions for reconstitution and/or use. For example, the label may indicate that the lyophilized formulation is to be reconstituted to amounts or concentrations of the active agent as described above. The label may further indicate that the formulation is useful or intended for subcutaneous or intramuscular administration, or other suitable method of administration. The container holding the formulation may be a multi-use vial, which allows for repeat administrations (e.g., from 2-6 administrations) of the reconstituted formulation. The kit may further comprise a second container comprising a suitable pharmaceutically-acceptable diluent, or other compound disclosed herein. The kit may further include other materials desirable from a commercial and user standpoint, including other excipients, buffers, diluents, filters, needles, syringes, and package inserts with instructions for use.

In animal subjects, the immune response may be monitored by periodically bleeding the animal, separating the sera from the collected blood, and analyzing the sera in an immunoassay, such as an ELISA assay, to determine the specific antibody titer. When an adequate antibody titer is established, the animal subject may be bled periodically to accumulate the polyclonal antisera. Polyclonal antibodies that bind specifically to the immunogen(s) may then be purified from immune antisera, for example, by affinity chromatography using protein A or protein G immobilized on a suitable solid support, as understood by persons having ordinary skill in the art. Affinity chromatography may be performed wherein an antibody specific for an Ig constant region of the particular immunized animal subject is immobilized on a suitable solid support. Affinity chromatography may also incorporate use of one or more immunogenic peptides, or fusion proteins, which may be useful for separating polyclonal antibodies by their binding activity to a particular immunogenic peptide. Monoclonal antibodies that specifically bind to an immunogenic peptide and/or fusion protein and immortal eukaryotic cell lines (e.g., hybridomas) that produce monoclonal antibodies having the desired binding specificity, may also be prepared, for example, using the technique of Kohler and Milstein ((Nature, 256:495-97 (1976), Eur. J. Immunol. 6:511-19 (1975)) and improvements thereto.

The term "homologous" or "% identity" as used herein means a nucleic acid (or fragment thereof) or an amino acid sequence (peptide or protein) having a degree of homology to the corresponding reference (e.g., wild type) nucleic acid, peptide or protein that may be equal to or greater than 70%, or equal to or greater than 80%, or equal to or greater than 85%, or equal to or greater than 86%, or equal to or greater than 87%, or equal to or greater than 88%, or equal to or greater than 89%, or equal to or greater than 90%, or equal to or greater than 91%, or equal to or greater than 92%, or equal to or greater than 93%, or equal to or greater than 94%, or equal to or greater than 95%, or equal to or greater than 96%, or equal to or greater than 97%, or equal to or greater than 98%, or equal to or greater than 99%. For example, in regard to peptides or polypeptides, the percentage of homology or identity as described herein is typically calculated as the percentage of amino acid residues found in the smaller of the two sequences which align with identical amino acid residues in the sequence being compared, when four gaps in a length of 100 amino acids may be introduced to assist in that alignment (as set forth by Dayhoff, in Atlas of Protein Sequence and Structure, Vol. 5, p. 124, National Biochemical Research Foundation, Washington, D.C. (1972)).

In one embodiment, the percentage homology as described above is calculated as the percentage of the components found in the smaller of the two sequences that may also be found in the larger of the two sequences (with the introduction of gaps), with a component being defined as a sequence of four, contiguous amino acids. Also included as substantially homologous is any protein product which may be isolated by virtue of cross-reactivity with antibodies to the native protein product. Sequence identity or homology can be determined by comparing the sequences when aligned so as to maximize overlap and identity while minimizing sequence gaps. In particular, sequence identity may be determined using any of a number of mathematical algorithms A non-limiting example of a mathematical algorithm used for comparison of two sequences is the algorithm of Karlin & Altschul, Proc. Natl. Acad. Sci. USA 1990, 87, 2264-2268, modified as in Karlin & Altschul, Proc. Natl. Acad. Sci. USA 1993, 90, 5873-5877. In at least one embodiment "% identity" represents the number of amino acids or nucleotides which are identical at corresponding positions in two sequences of a protein having the same activity or encoding similar proteins. For example, two amino acid sequences each having 100 residues will have 95% identity when 95 of the amino acids at corresponding positions are the same. Similarly, two amino acid sequences each having 100 residues will have at least 90% identity when at least 90 of the amino acids at corresponding positions are the same. Similarly, two amino acid sequences each having 20 residues will have 95% identity when 19 of the amino acids at corresponding positions are the same, or 90% identity when at least 18 of the amino acids at corresponding positions are the same, or 85% identity when at least 17 of the amino acids at corresponding positions are the same, or 80% identity when at least 16 of the amino acids at corresponding positions are the same.

Further, where a sequence is described herein as having "at least X % identity to" a reference sequence, this is intended to include, unless indicated otherwise, all percentages greater than X %, such as for example, (X+1)%, (X+2)%, (X+3)%, (X+4)%, and so on, up to 100%.

Another example of a mathematical algorithm used for comparison of sequences is the algorithm of Myers & Miller, CABIOS 1988, 4, 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988, 85, 2444-2448.

Another algorithm is the WU-BLAST (Washington University BLAST) version 2.0 software (WU-BLAST version 2.0 executable programs for several UNIX platforms). This program is based on WU-BLAST version 1.4, which in turn is based on the public domain NCBI-BLAST version 1.4 (Altschul & Gish, 1996, Local alignment statistics, Doolittle ed., Methods in Enzymology 266, 460-480; Altschul et al., Journal of Molecular Biology 1990, 215, 403-410; Gish & States, Nature Genetics, 1993, 3: 266-272; Karlin & Altschul, 1993, Proc. Natl. Acad. Sci. USA 90, 5873-5877; all of which are incorporated by reference herein).

In addition to those otherwise mentioned herein, mention is made also of the programs BLAST, gapped BLAST, BLASTN, BLASTP, and PSI-BLAST, provided by the National Center for Biotechnology Information. These programs are widely used in the art for this purpose and can align homologous regions of two amino acid sequences. In all search programs in the suite, the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, references to a segment in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc. Acids Res. 12:387-395 (1984).

Another example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. Software for performing BLAST analyses is publicly available through the National Center for Biotechnology Information (website at www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0).

For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The terms "polynucleotide sequence" or "nucleic acid," as used herein, include any polynucleotide sequence which encodes a peptide or fusion protein (or polypeptide) including polynucleotides in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand. The polynucleotide sequence encoding a peptide or fusion protein, or encoding a therapeutically-effective variant thereof can be substantially the same as the coding sequence of the endogenous coding sequence as long as it encodes an immunogenically-active peptide or fusion protein. Further, the peptide or fusion protein may be expressed using polynucleotide sequence(s) which differ in codon usage due to the degeneracies of the genetic code or allelic variations. Moreover, the peptides and fusion proteins of the present disclosure and the nucleic acids which encode them include peptide/protein and nucleic acid variants which comprise additional substitutions (conservative or non-conservative). For example, the immunogenic peptide variants include, but are not limited to, variants that are not exactly the same as the sequences disclosed herein, but which have, in addition to the substitutions explicitly described for various sequences listed herein, additional substitutions of amino acid residues (conservative or non-conservative) which substantially do not impair the activity or properties of the variants described herein. Examples of such conservative amino acid substitutions may include, but are not limited to, ala to gly, ser, or thr; arg to gln, his, or lys; asn to asp, gln, his, lys, ser, or thr; asp to asn or glu; cys to ser; gln to arg, asn, glu, his, lys, or met; glu to asp, gln, or lys; gly to pro or ala; his to arg, asn, gln, or tyr; ile to leu, met, or val; leu to ile, met, phe, or val; lys to arg, asn, gln, or glu; met to gln, ile, leu, or val; phe to leu, met, trp, or tyr; ser to ala, asn, met, or thr; thr to ala, asn, ser, or met; trp to phe or tyr; tyr to his, phe or trp; and val to ile, leu, or met.

The terms "infection," "transduction," and "transfection" are used interchangeably herein and mean introduction of a gene, nucleic acid, or polynucleotide sequence into cells such that the encoded protein product is expressed. The polynucleotides may comprise additional sequences, such as additional coding sequences within the same transcription unit, controlling elements such as promoters, ribosome binding sites, transcription terminators, polyadenylation sites, additional transcription units under control of the same or different promoters, sequences that permit cloning, expression, homologous recombination, and transformation of a host cell, and any such construct as may be desirable to provide embodiments of the present disclosure.

In certain embodiments, the present disclosure includes expression vectors capable of expressing one or more polypeptides. Expression vectors for different cell types are well known in the art and can be selected without undue experimentation. The DNA encoding the polypeptide is inserted into an expression vector, such as a plasmid, in proper orientation and correct reading frame for expression. If necessary, the DNA may be operably-linked to the appropriate transcriptional and translational regulatory control nucleotide sequences such as promoters and/or enhancers recognized by the desired host, although such controls are generally available in the expression vector. The vector is then introduced into the host through standard techniques. Guidance can be found e.g., in Sambrook et al. Molecular Cloning: A Laboratory Manual, 3d ed., Cold Spring Harbor Laboratory Press, N Y 2001)).

EXAMPLES

The immunogenic compositions and vaccines and methods of their use having now been generally described, will be more readily understood by reference to the following examples and embodiments, which are not intended to be limiting. The following detailed examples and methods describe how to make and use the various immunogenic compositions of the present disclosure and are to be construed, as noted above, only as illustrative. Those skilled in the art will promptly recognize appropriate variations from the compositions and procedures.

Materials and Methods

Statistical analysis. Results were analyzed using either one-way analysis of variance (ANOVA), two-way ANOVA, or non-parametric one-way ANOVA on ranks, followed by Bonferroni's or Dunn's multiple comparisons posttest when appropriate using the statistical software program Prism.

Cloning, construction of TcdB deletion mutants, and protein purification. Recombinant TcdB2 was expressed in a *Bacillus megaterium* system (MoBiTec, Göttingen, Germany) as described in Larabee et al., 2015 (Larabee J L, Krumholz A, Hunt J J, Lanis J M, Ballard J D. 2015. Exposure of neutralizing epitopes in the carboxyl-terminal domain of TcdB is altered by a proximal hypervariable region. J Biol Chem 290:6975-6985), and affinity purified by $Ni^{2+}$ chromatography. Mutations in tcdB2 (pC-His1522-

TcdB2) were made using the QuikChange II XL Site-Directed Mutagenesis kit (Agilent, catalog #200523), by addition of a pair of primers with sequences flanking the regions targeted for deletion. Mutants were verified for the appropriate deletion and the absence of off-target mutations by DNA sequencing.

Cell culture. The hamster epithelial cell line CHO-K1 and the human cervical epithelial cell line HeLa were purchased from American Type Culture Collection (ATCC). CHO-K1 cells were cultured in F12-K media supplemented with 10% fetal bovine serum (FBS), and 100 units/ml penicillin, and 100 µg/ml streptomycin. HeLa cells were cultured in DMEM media supplemented with 10% FBS and 100 units/ml penicillin, and 100 µg/ml streptomycin. All cells were grown at 37° C. in the presence of 5% CO2.

Glucosyltransferase activity assay. Glucosyltransferase activity was measured in a cell free assay. A range of toxin concentrations (2.5 nM-25 nM) were incubated with 400 nM of GST-Rac1, either with or without 40 µM UDP-glucose. The reactions were carried out at 37° C. for 60 min in a buffer comprised of 50 mM HEPES (pH 7.5), 100 mM KCl, 2 mM $MgCl_2$, 1 mM MnCl2, and 100 µg/ml BSA. The reaction was stopped by heating the sample at 95° C. for 7 min in SDS-PAGE sample buffer (62.5 mm Tris-HCl (pH 6.8), 2% SDS, 10% glycerol, 5% β-mercaptoethanol, and 0.001% bromphenol blue). Twenty-five percent of each reaction was then resolved on SDS-PAGE (12%) before being transferred to PVDF membrane for blotting. Glucosylation was detected using an antibody that specifically recognizes non-glucosylated Rac1 (BD Bioscience, catalog number: 610651). A second antibody against total Rac1 (Millipore Sigma, catalog number: 05-389) was used to ensure samples contained similar amounts of Rac1. Primary antibodies were incubated with membranes overnight, at 4° C., before membranes were washed and probed with an HRP-conjugated secondary antibody for 15 min Blots were developed using a chemiluminescent enhancement system (Bio-Rad, catalog number: 1705061) and then visualized using the Bio-Rad ChemiDocMP system.

Autoprocessing assay. Autoprocessing in TcdB2 and $TcdB2_{\Delta1769-1787}$ was assessed by incubating 5 µg of the respective protein with 25, 50, or 100 µM of inositol hexakisphosphate overnight at 37° C. in 20 mM Tris, pH 8. The reaction was stopped by addition of SDS-PAGE sample buffer and heated at 95° C. for 7 min, before the sample was resolved on SDS-PAGE (8%). The extent of autoprocessing was assessed by either coomassie staining or immunoblot analysis. An antibody against the amino-terminus of TcdB (R&D Biosystems, catalog number: AF6246) was used for the immunoblot. Blots were developed using a chemiluminescent enhancement system (Bio-Rad, catalog number: 1705061), and imaged using the Bio-Rad ChemiDocMP system. Densitometry analysis was carried out using ImageJ.

ELISA. Thermo Scientific Pierce 96-well microplates (catalog number: PI15041) were coated with TcdB at 10 µg/ml in binding buffer (0.1 M $Na_2HPO_4$) overnight at 4° C. Plates were then washed and blocked with 1.0% w/v BSA in PBS/0.05% v/v Tween 20 for 2 h at room temperature before washing. Sera was diluted in PBS/0.05% v/v Tween 20, and applied overnight at 4° C. The plates were then washed the following day, and HRP-conjugated anti-mouse IgM or IgG1 at 0.2 µg/ml was applied for 1 h at room temp. 90 µl ABTS developer (Seracare, catalog number: 5120-0035) was then added to each well for 3 min. Color development was halted by addition of 110 µl of stop solution (10% w/v SDS solution). Absorbance was read at 405 nm, and endpoint titers were determined as [(Abs. sample)−(average Abs. blank wells+two standard deviations)], with the endpoint titer being set as the dilution at which the absorbance value fell below 0 after the above calculation.

Cell viability assay. Viability of cells after toxin exposure was assessed using a tetrazolium salt based assay Cell Counting Kit-8 (Dojindo Molecular Technologies, Inc. catalog number: CK04-05). Cells were seeded in 96-well plates (Grenier Bio-One, catalog number: 655180) at a density of $1 \times 10^4$ cells per well in 100 and incubated overnight at 37° C. to allow cells to grow to approximately 80% confluence. Cells were then treated with toxin 24 h after plating, with concentrations ranging from 0.001-1000 pM. Toxins were left on cells overnight at 37° C., before CCK-8 media was applied. CHO cells were incubated with 5% CCK-8 solution in cell culture media for 4 h before absorbance was measured at 450 nm. Viability was calculated as ((Abs. treated cells/Abs. untreated cells)×100), using normalized absorbance values.

TcdB cell association assay. Cells were seeded into 12-well plates (Costar, catalog number: 3513) at a density of $5 \times 10^5$ cells per well in 1 ml of cell culture media, and incubated overnight at 37° C. Cells were then washed three times with PBS, before 900 µl of fresh media was applied. Plates were returned to 37° C. for 1 h, before 100 µl of 1 µg/ml toxin was applied (diluted in cell media), for a final concentration of 100 ng/ml. Plates were again returned to 37° C. for 1 h, before being washed three times with 4° C. PBS to remove unbound toxin. Following washing, cells were lysed by addition of 150 µl of lysis buffer (1% SDS, 50 mM Tris, 5 mM EDTA). Plates were placed on ice for 15 min during lysis. Cell lysates were then collected and sonicated before protein concentration was determined by Lowry assay. 20 µg of total lysate protein was then resolved by SDS-PAGE (8%) under protein reducing conditions, before transfer to PVDF membrane. Membranes were blocked with 5% milk in wash buffer (Tris-buffered saline, 0.1% Tween-20), before being probed overnight with antibodies specific for TcdB (R&D Biosystems, catalog number: AF6246), or GAPDH (abcam, catalog number: ab8245) as a loading control. The membranes were then washed and incubated with HRP-conjugated secondary antibody at room temperature for 1 h. Blots were developed using a chemiluminescent enhancement system (Bio-Rad, catalog number: 1705061) before images were captured using the Bio-Rad ChemiDocMP system.

TcdB immunization. Six-week old female C57BL/6 mice were purchased from The Jackson Laboratory and housed in a pathogen-free facility. Mice were immunized between the ages of 8 to 10 weeks, with a subcutaneous injection divided between both rear flanks. Vaccines consisted of 50 µg of $TcdB2_{D270N}$ or $TcdB2_{\Delta1769-1787}$ in sterile PBS, adsorbed to Alhydrogel Alum (Invivogen, San Diego, Calif.) (33). Mice were vaccinated initially on day 0, followed by a booster at day 28. The booster consisted of 25 µg of antigen in sterile PBS, with no adjuvant. Retro-orbital or submandibular blood collections were done on days 14, 28 (pre-boost), 42 and then 2 weeks post-infection. Samples were allowed to incubate at room temperature for 4 h, before centrifugation at 15,000×g for 15 min to separate cells and debris from the serum. Sera was then aliquoted to a new tube and stored at −80° C.

C. difficile challenge. Between 14-20 d following booster, animals began a 5 d treatment with Cefoperazone (mpbio, catalog number: 02199695-CF) in sterile drinking water at a concentration of 0.5 mg/ml. Antibiotic water was switched out every other day, in accordance with the protocol published in Theriot C M, Koumpouras C C, Carlson P E, Bergin I I, Aronoff D M, Young V B. 2011. Cefoperazone-treated mice as an experimental platform to assess differential virulence of Clostridium difficile strains. Gut Microbes 2:326-334. The mice were then provided untreated drinking water for 2 d before oral gavage. Oral gavage contained between 1×10$^5$ spores hypervirulent *C. difficile* strain R20291 in 30 µl of PBS. Following *C. difficile* gavage, mice were weighed daily for 14 d to measure disease severity.

Fecal CFU determination. Fresh fecal samples were collected from mice at day 0, 2, 4, 7, and 10 post-gavage for analysis. Fecal pellets were diluted 1:10 (w/v) in PBS and incubated anaerobically for 30 min at 37° C. After 30 min, the pellet was disrupted into solution and serial 1:10 dilutions were made anaerobically. One-hundred microliters of each dilution was then transferred to Taurocholate Cycloserine Cefoxitin Fructose Agar (TCCFA) plates, and plates were incubated at 37° C. for 24 h before colonies were enumerated. Total CFU calculation was based on dilution factor and initial weight of feces collected. The dilution plate with the lowest countable number (between 20-200 colonies) was used for calculation of CFU/g of fecal content.

TcdB neutralization assay. CHO-K1 cells were seeded in 96-well plates (Grenier Bio-One, catalog number: 655180) at a density of 7.5×10$^3$ cells per well in 100 and incubated overnight at 37° C. Sera from mice was diluted 1/100 in cell culture media, and mixed with TcdB2 in cell culture media for a final toxin concentration of 1 pM. The toxin concentration was chosen as it causes 100% cell rounding, and leaves approximately 20% viable cells as measured by CCK-8 assay. The serum/toxin mixture was incubated for 1 h at room temperature, before medium was removed from CHO cells and replaced with either serum/toxin mixture, or toxin alone. Following an overnight incubation at 37° C., a 5% CCK-8 solution was applied to the cells for 4 h before absorbance was measured at 450 nm. Viability was calculated as ((Abs. treated cells/Abs. untreated cells)×100), using normalized absorbance values.

Differential scanning fluorimetry. Thermal melting temperature ($T_m$) of the toxins was measured by combining purified TcdB2 or TcdB2$_{\Delta1769\text{-}1787}$ with SYPRO orange fluorescent dye, in quadruplicate. The fluorescence emission was monitored over a temperature gradient of 25° C.-99° C., using an Applied Biosystems 7500 real-time PCR system. The reactions were performed in a buffer comprised of 20 mM HEPES (pH 8) and 150 mM NaCl. The $T_m$ value was calculated by graphing the first derivative of the melting curve, with the $T_m$ being equivalent to the midpoint of the transition from folded to unfolded.

Protein labeling with Alexa Fluor™ 488. Proteins were fluorescently labeled on primary amines using the Alexa Fluor™ 488 Protein Labeling Kit from Molecular Probes (catalog number: A10235), according to the manufacturer's directions. Dye incorporation for TcdB2 was approximately 1 mole of dye per mole of protein, while the incorporation for TcdB2$_{\Delta1769\text{-}1787}$ was approximately 2.3 moles of dye per mole of protein.

Fluorescence microscopy. CHO-K1 cells were seeded into a 96-well plate (Grenier Bio-One, catalog number: 655180) at a density of 8×10$^4$ cells/ml and incubated at 37° C. overnight to allow adherence. After overnight incubation, cells were treated in triplicate with Alexa-Fluor™ 488 labeled TcdB2 or TcdB2$_{\Delta1769\text{-}1787}$, and cell association was visualized using an Olympus IX51 Inverted Microscope (Olympus, Waltham, Mass.). The experiment was repeated three times, and greater than 10 fields per well were examined for fluorescence.

Results

Internal deletion mutants disrupt cytotoxicity of TcdB2. A series of variants of TcdB2 with deletions in the 1753-1852 region were constructed, expressed, and purified (FIG. 1A). To ensure any effects seen were a result of deletions in this specific region, a control variant (TcdB2$_{\Delta2213\text{-}2223}$) with a 10-amino acid portion of the CROP domain (amino acids 2213-2223), with no reported function, was deleted from the toxin. Following purification, each mutant was analyzed by SDS-PAGE and Coomassie staining (FIG. 1B). Deletion mutants TcdB2$_{\Delta1769\text{-}1779}$, TcdB2$_{\Delta1769\text{-}1787}$, TcdB2$_{\Delta1847\text{-}1856}$ and TcdB2$_{\Delta1751\text{-}1761}$ migrated as multiple bands, and included bands at approximately 270 kDa and 200 kDa.

The impact of the various TcdB2 deletion mutants on cell viability was determined using CHO-K1 cells and a tetrazolium salt based assay, which measures the extent of dehydrogenase activity in cells. The amount of the colorimetric formazan-dye produced by cell dehydrogenase activity is in direct proportion to the number of living, metabolically active cells. As shown in FIG. 1C, cell viability did not change following treatment with TcdB2$_{\Delta1769\text{-}1779}$ or TcdB2$_{\Delta1769\text{-}1787}$. TcdB2$_{\Delta1751\text{-}1761}$, TcdB2$_{\Delta1847\text{-}1856}$, and TcdB2$_{\Delta1847\text{-}1866}$ exhibited an EC$_{50}$ between 50 and 100 pM. Treatment with TcdB2$_{\Delta1773\text{-}1774}$ and TcdB2$_{\Delta2213\text{-}2223}$, or TcdB alone resulted in an EC$_{50}$ between 10 and 100 fM. Of the mutants tested, only cells treated with TcdB2$_{\Delta1769\text{-}1787}$ showed no loss in cell viability at the highest concentration tested. This observation held true even when cells were exposed to TcdB2$_{\Delta1769\text{-}1787}$ at a final concentration of 1 µM (data not shown).

Figure 2B:
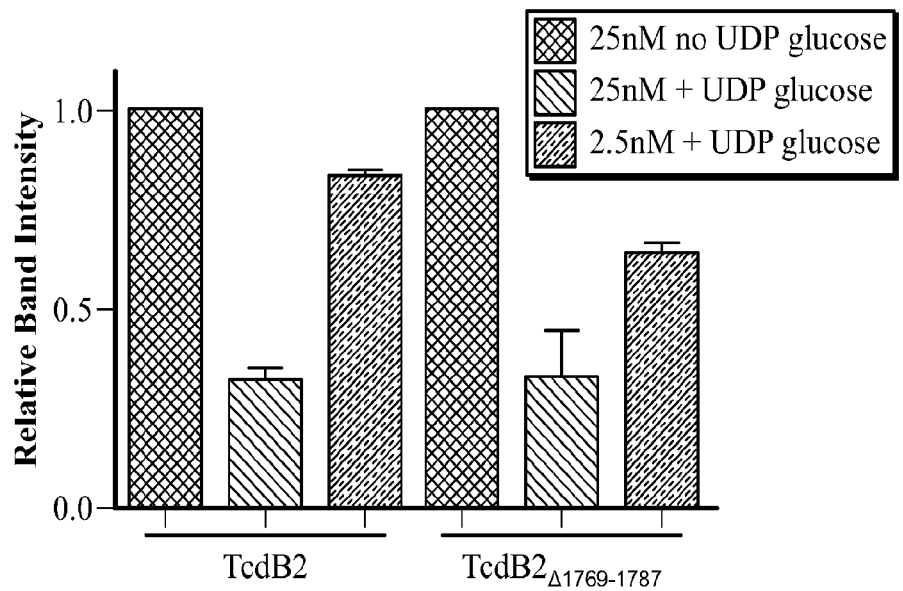

TcdB2 deletion mutant retains glucosylation activity. Previous work has suggested that the efficiency of glucosylation of TcdA and TcdB is hindered by conformational restrictions within the proteins. It was therefore predicted that deletions which remove conformational constraints in TcdB could result in forms of the protein with altered glucosylation activity. As a quantitative test of glucosylation activity, TcdB2$_{\Delta1769\text{-}1787}$ and TcdB2 were incubated with the GTPase Rac1, and UDP-glucose, both substrates of TcdB. Glucosylation of Rac1 was then examined by immunoblot using an antibody that recognizes only substrate which has not been glucosylated. A reduction in signal therefore correlates with glucosylation of the substrate, Rac1. TcdB2$_{\Delta1769\text{-}1787}$ was seen to exhibit glucosylation activity equal to that of wild-type TcdB2 (FIG. 2A-B), indicating the reduction in cytotoxicity is not due to a loss in glucosyltransferase activity.

Figure 3A:
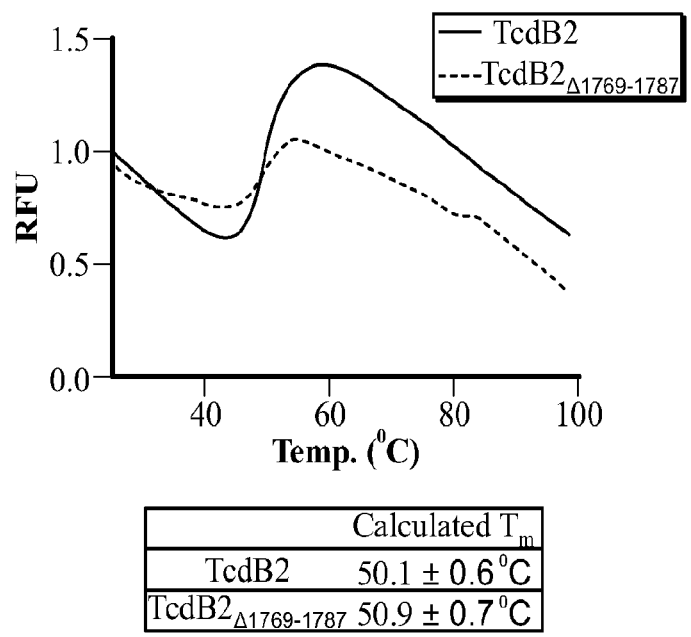
FIG. 3A shows a Differential Scanning Fluorimetry profile of TcdB2 and TcdB2$_{\Delta1769-1787}$ (0.1 mg/mL) incubated in the presence of SYPRO-Orange across a temperature gradient (25° C.-99° C.). Increase in fluorescence corresponds to protein unfolding and exposure of hydrophobic domains. The first derivative of the profile was used to calculate the melting temperature ($T_m$). Results are given as mean±standard deviation.
Figure 3B:
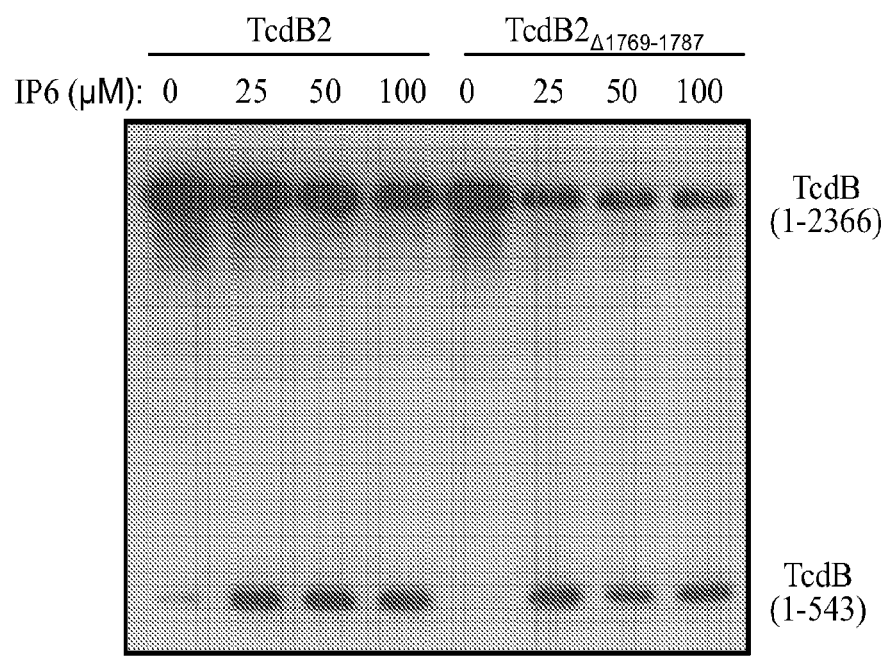
FIG. 3B shows immunoblot analysis of in-vitro IP-6 induced autoprocessing. TcdB2 and TcdB2$_{\Delta1769-1787}$ were incubated with IP6 (0, 25, 50, and 100 µM) overnight before samples were analyzed by immunoblot.
Figure 3C:
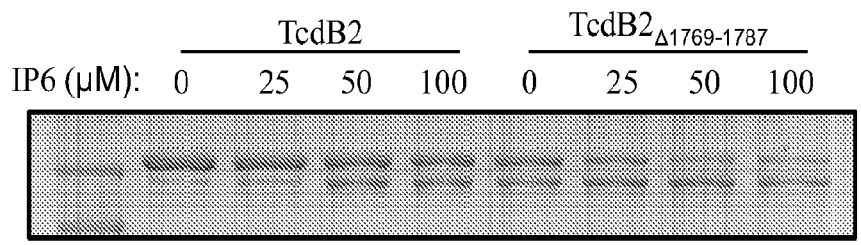
FIG. 3C shows Coomassie stained SDS-PAGE (8%) of in vitro autoprocessing samples of TcdB2 and TcdB2$_{\Delta1769-1787}$.
Figure 3D:
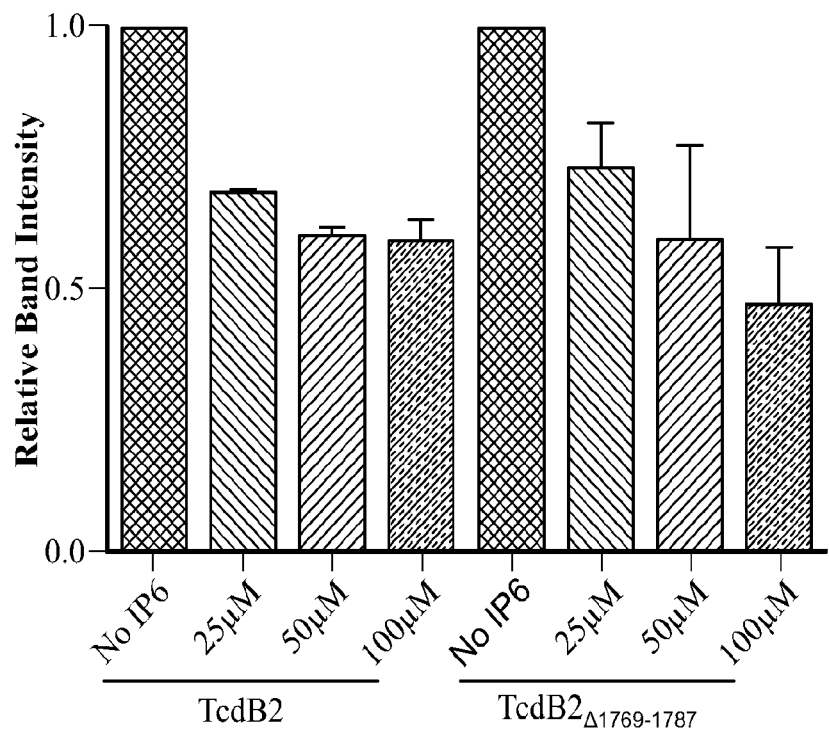
FIG. 3D shows a bar graph presenting densitometry analysis of three independent autoprocessing experiments for TcdB2 and TcdB2$_{\Delta1769-1787}$. Results are given as mean±standard deviation, significance determined by one-way ANOVA on ranks.
Figure 3E:
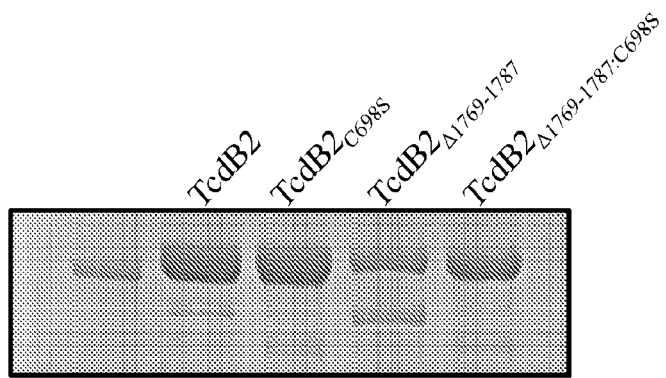
FIG. 3E shows Coomassie stained SDS-PAGE (8%) showing TcdB2, TcdB2$_{C698S}$, TcdB2$_{\Delta1769-1787}$, and TcdB2$_{\Delta1769-1787,C698S}$.
Figure 3F:
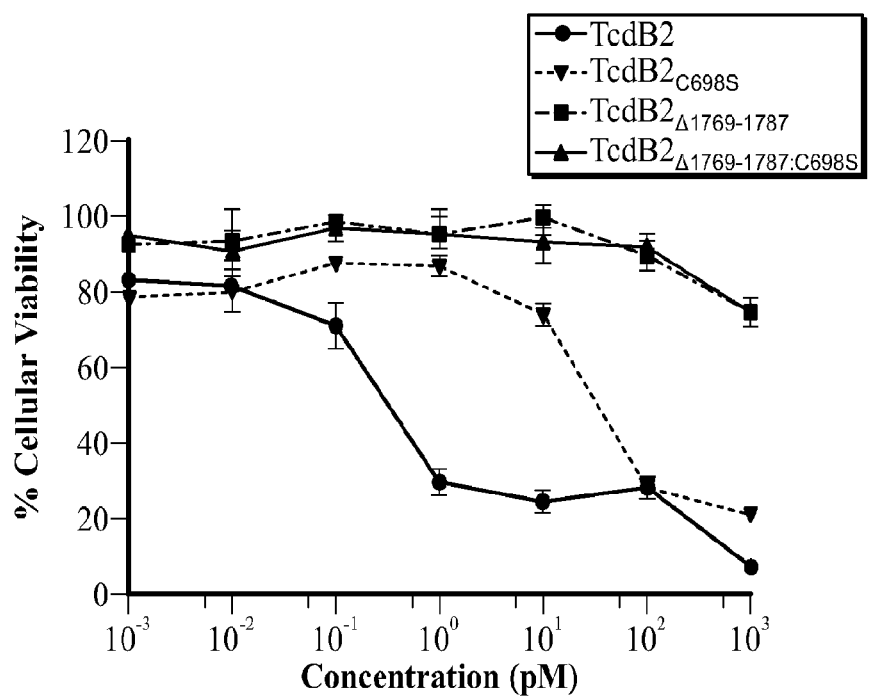
FIG. 3F shows results of a cytotoxicity assay showing cellular viability of CHO-K1 cells after 24 h treatment with TcdB2, TcdB2$_{C698S}$, TcdB2$_{\Delta1769-1787}$, and TcdB2$_{\Delta1769-1787,C698S}$ Data are presented as mean±standard deviation.
Figure 4A:
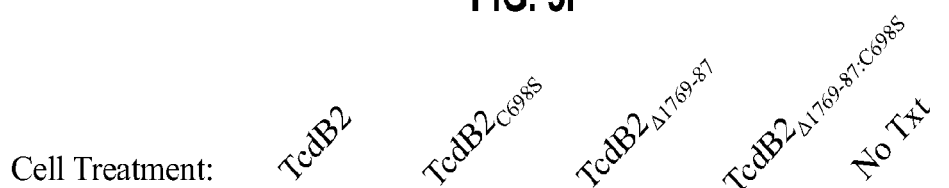
FIG. 4A is an immunoblot analysis showing cell association of TcdB2 and various TcdB2 mutants with CHO-K1 cells following 1 h incubation at 37° C. The cells were then washed repeatedly to remove unbound toxin, and cell lysates were analyzed by immunoblot.
Figure 4A:
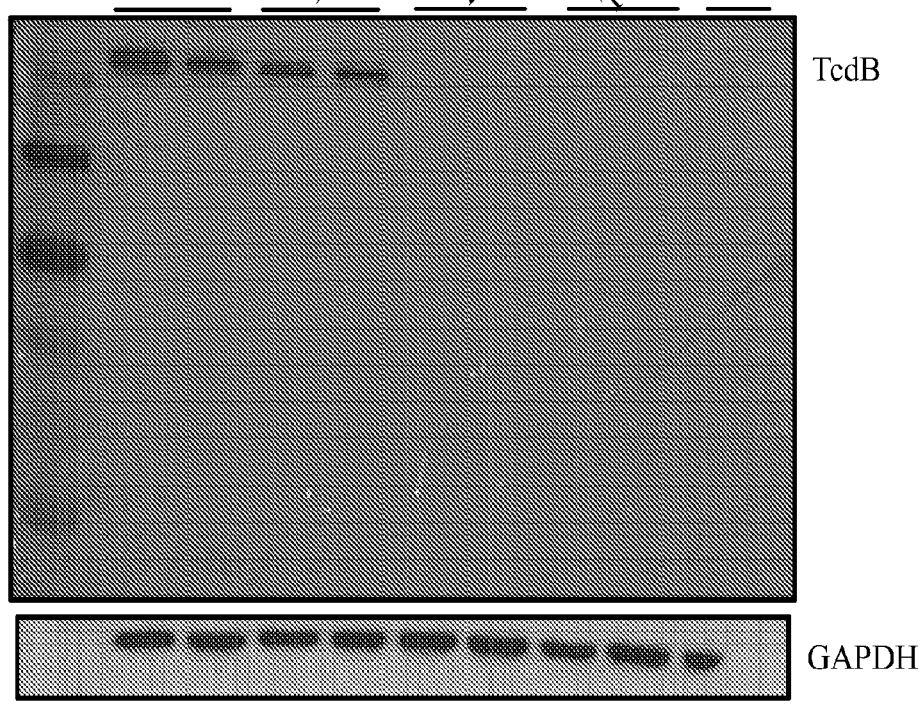
Figure 4B:
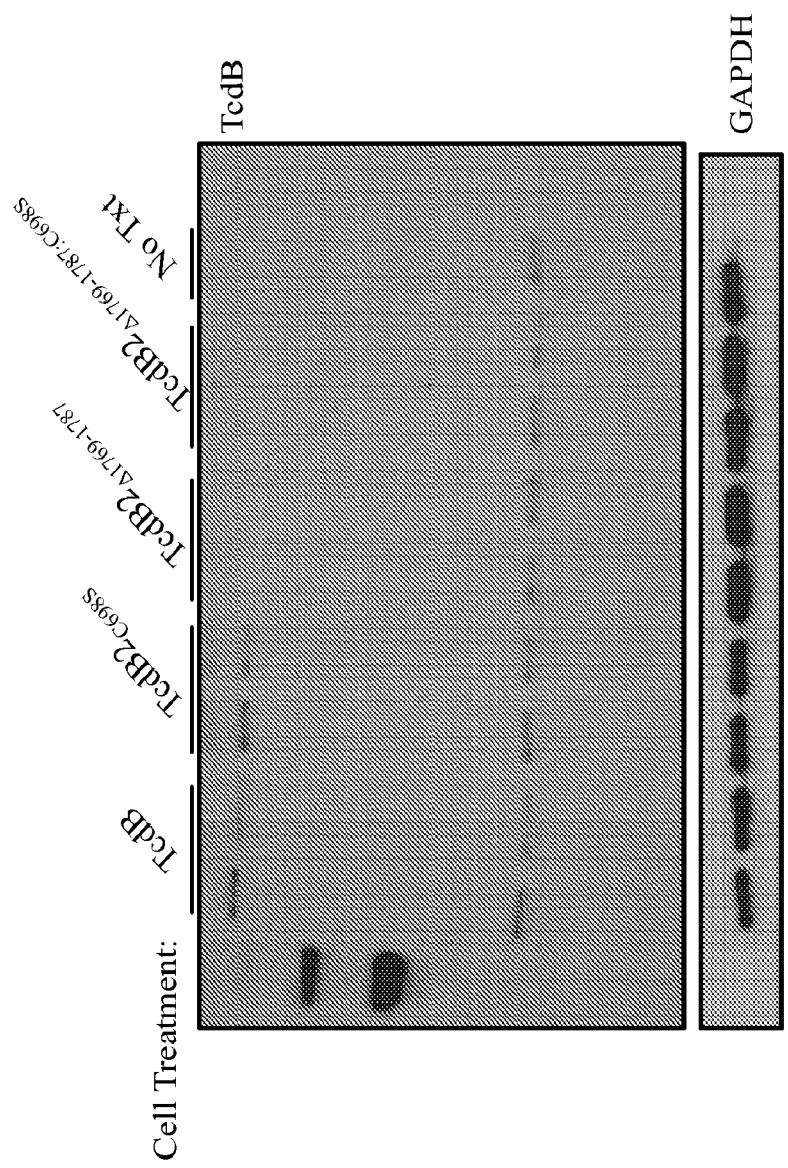
FIG. 4B is an immunoblot analysis showing cell association of TcdB2 and various TcdB2 mutants with HeLa cells following 1 h incubation at 37° C. The cells were then washed repeatedly to remove unbound toxin, and cell lysates were analyzed by immunoblot.
Figure 4C:
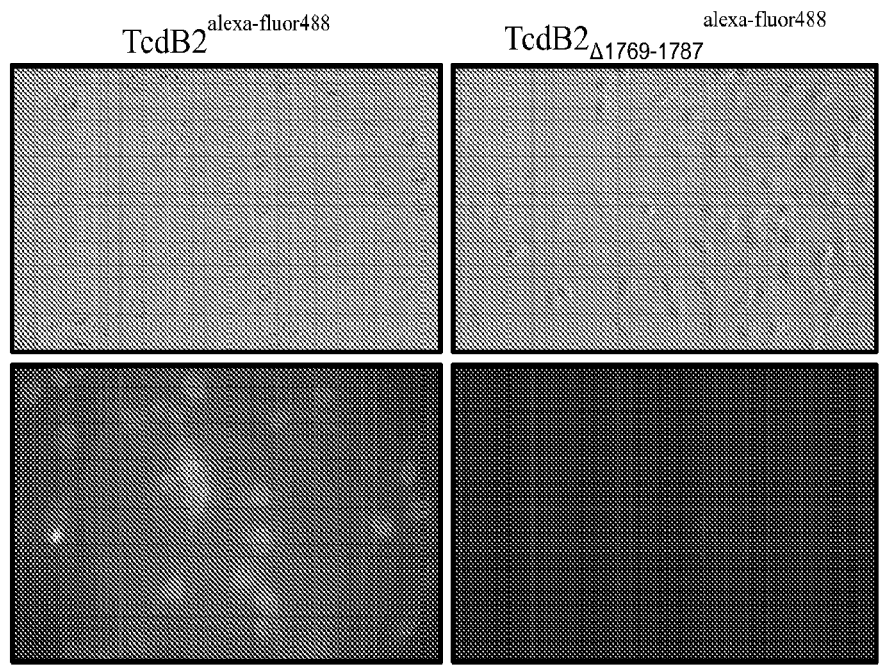
FIG. 4C shows representative fluorescence microscopy images showing CHO-K1 cells treated with Alexa Fluor-488 labeled TcdB2 or Alexa Fluor-488 labeled TcdB2$_{\Delta1769-1787}$.
Figure 5A:
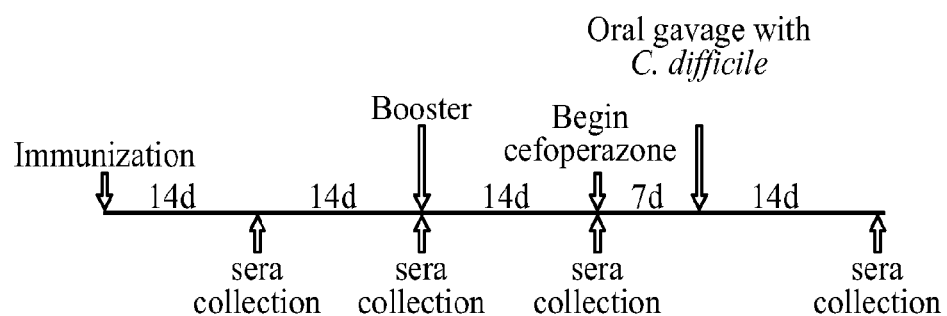
FIG. 5A shows a schematic layout of a murine experimental vaccination schedule with TcdB$_{\Delta1769-1787}$ in a murine model of CDI.
Figure 5B:
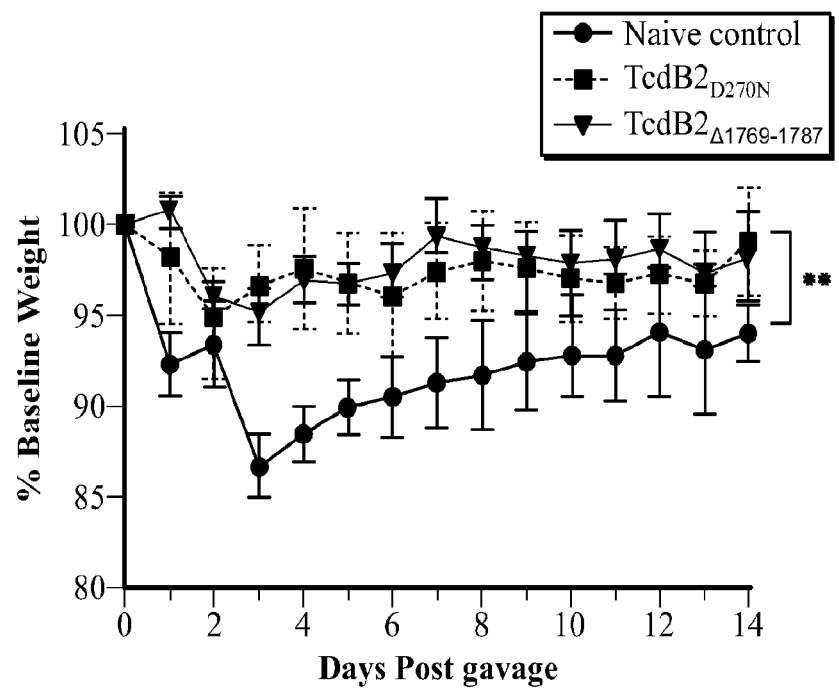
FIG. 5B is a graph summarizing results of weight loss data for control and experimental vaccination animals treated according to the schedule of FIG. 5A Animals were weighed every 24 h for 14 d following oral gavage with *C. difficile* spores. The pre-gavage weight of each individual animal was set as the baseline weight (100%) and subsequent weight loss was calculated as a percentage of the baseline weight. Data are presented as mean±standard deviation (n=5, representative of two independent experiments). Statistical significance was determined by two-way ANOVA and Dunnett's posttest, with asterisks indicating significant differences in percent baseline weight versus the control. **, $P \leq 0.01$ at all timepoints.
Figure 5C:
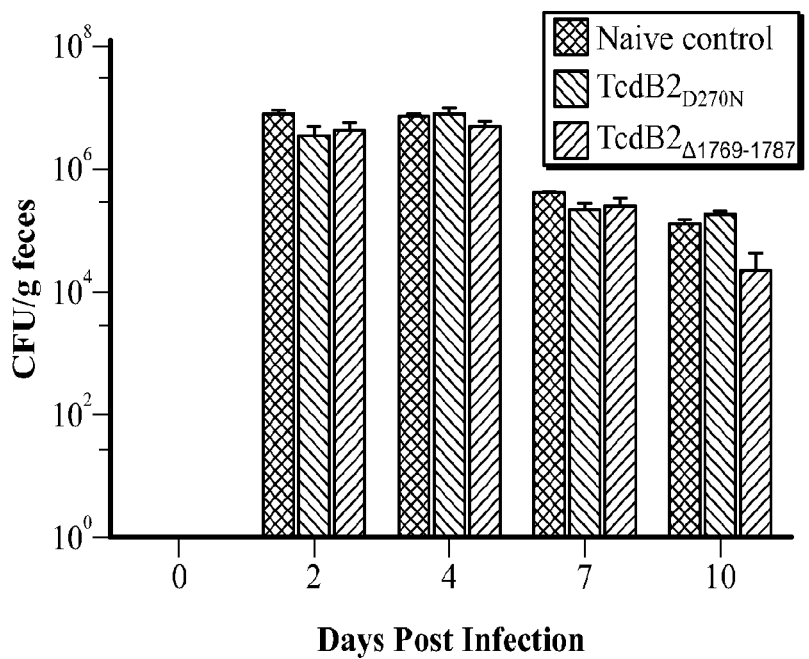
FIG. 5C is a graph summarizing results of fecal CFUs during infection in the experimental vaccination animals treated according to the schedule of FIG. 5A. Fecal samples were collected from mice at d 0, 2, 4, 7, and 10 post-gavage for analysis. Data are presented as mean±standard deviation, with significance determined by two-way ANOVA and Dunnett's posttest.
Figure 5D:
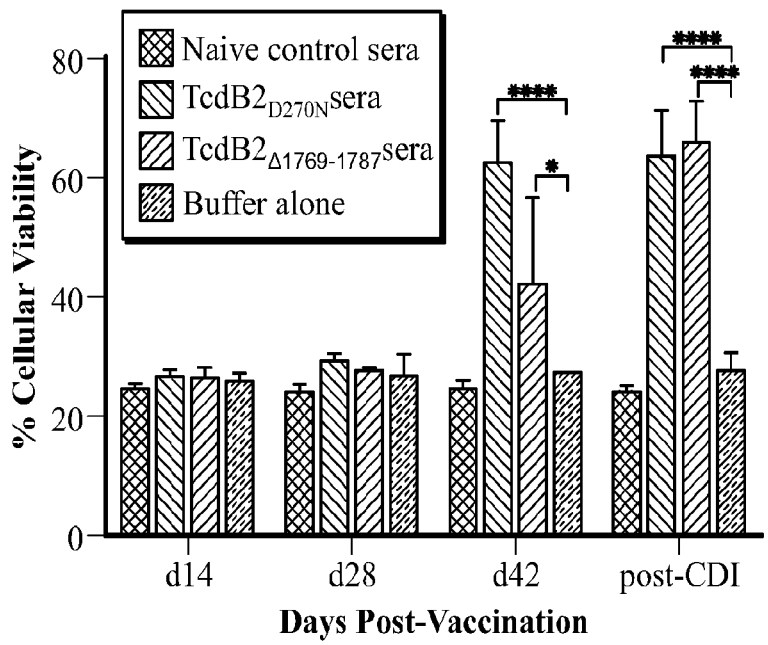
FIG. 5D shows results of a cytotoxicity assay showing cellular viability of CHO-K1 cells following 24 h treatment with TcdB2 in the presence or absence of sera from vaccinated mice. Results are given as mean±standard deviation, with significance determined by two-way ANOVA and Dunnett's posttest. *, $P \leq 0.05$; ****, $P \leq 0.0001$. Data are representative of three independent experiments.
Figure 6A:
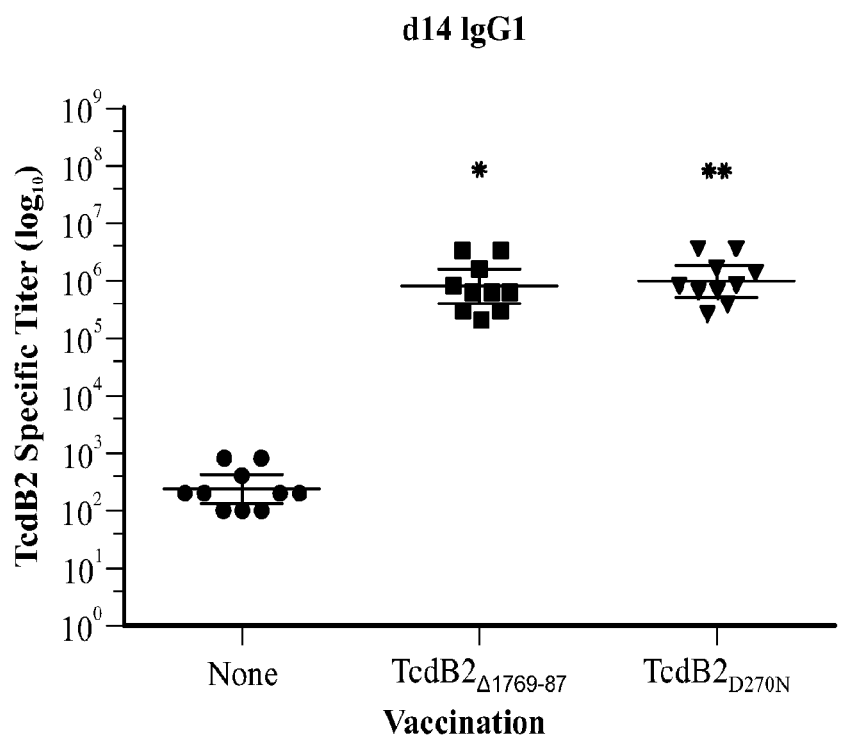
FIG. 6A shows results of the immune response to vaccination with TcdB2$_{\Delta1769-1787}$. Sera was collected at the 14 day time-point indicated in FIG. 5A. TcdB2 specific IgG1 titers were determined by ELISA. Each data point represents one individual animal, and bars display geometric mean±standard deviation for the group. Statistical significance was determined by ANOVA or one-way ANOVA on ranks followed by Dunnett's or Dunn's posttest, with asterisks indicating significant titer increases versus the control. *, $P \leq 0.05$; , $P \leq 0.01$; *, $P \leq 0.001$; ns, $P \geq 0.05$. Data are pooled from independent experiments.
Figure 6B:
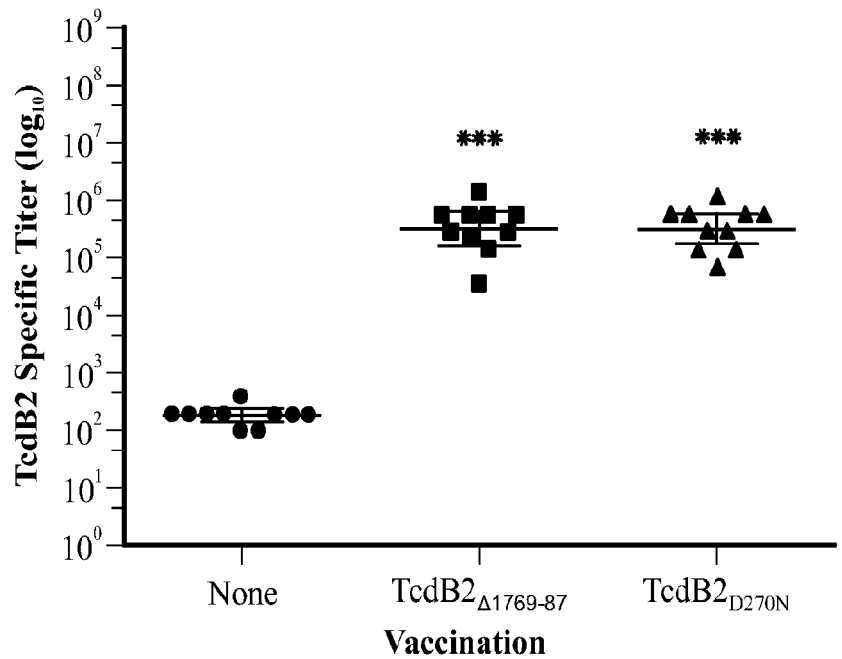
FIG. 6B shows results of the immune response to vaccination with TcdB2$_{\Delta1769-1787}$. Sera was collected at the 28 day time-point indicated in FIG. 5A. TcdB2 specific IgG1 titers were determined by ELISA. Each data point represents one individual animal, and bars display geometric mean±standard deviation for the group. Statistical significance was determined by ANOVA or one-way ANOVA on ranks followed by Dunnett's or Dunn's posttest, with asterisks indicating significant titer increases versus the control. *, $P \leq 0.05$; , $P \leq 0.01$; *, $P \leq 0.001$; ns, $P \geq 0.05$. Data are pooled from independent experiments.
Figure 6C:
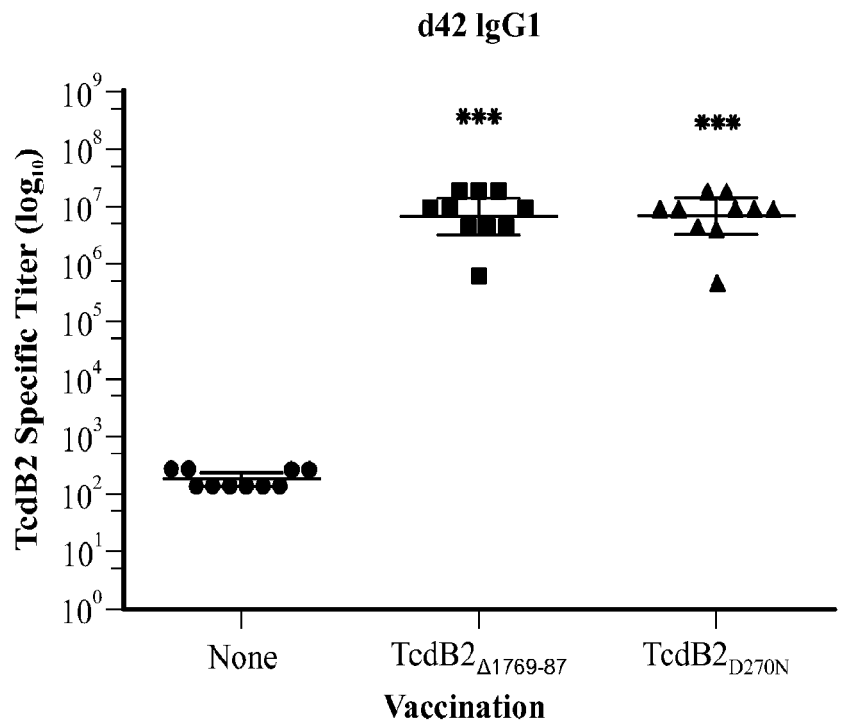
FIG. 6C shows results of the immune response to vaccination with TcdB2$_{\Delta1769-1787}$. Sera was collected at the 42 day time-point indicated in FIG. 5A. TcdB2 specific IgG1 titers were determined by ELISA. Each data point represents one individual animal, and bars display geometric mean±standard deviation for the group. Statistical significance was determined by ANOVA or one-way ANOVA on ranks followed by Dunnett's or Dunn's posttest, with asterisks indicating significant titer increases versus the control. *, $P \leq 0.05$; , $P \leq 0.01$; *, $P \leq 0.001$; ns, $P \geq 0.05$. Data are pooled from independent experiments.
Figure 6D:
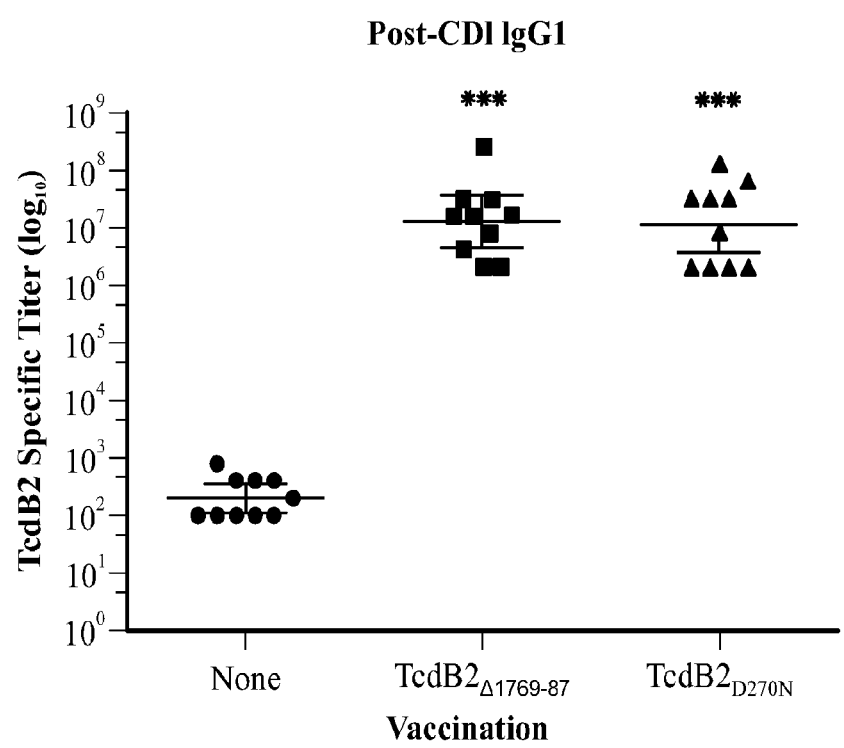
FIG. 6D shows results of the immune response to vaccination with TcdB2$_{\Delta1769-1787}$. Sera was collected at the final time-point indicated in FIG. 5A. TcdB2 specific IgG1 titers were determined by ELISA. Each data point represents one individual animal, and bars display geometric mean± standard deviation for the group. Statistical significance was determined by ANOVA or one-way ANOVA on ranks followed by Dunnett's or Dunn's posttest, with asterisks indicating significant titer increases versus the control. *, $P \leq 0.05$; , $P \leq 0.01$; *, $P \leq 0.001$; ns, $P \geq 0.05$. Data are pooled from independent experiments.

Thermal transition profile of TcdB2$_{\Delta1769\text{-}1787}$ is similar to TcdB2. Though the results from the glucosylation assay suggested the structure of TcdB2$_{\Delta1769\text{-}1787}$ had not changed in a way that alters enzymatic activity, we performed a second experiment to measure the structural stability of this mutant in comparison to TcdB2. The thermal stability across a gradient of increasing temperature was determined for TcdB2$_{\Delta1769\text{-}1787}$ by calculating the thermal denaturation temperature, which was then compared to that of TcdB2. Differential scanning fluorimetry was used to measure temperature-induced unfolding and exposure of hydrophobic domain. Fluorescence emission profiles across a temperature gradient from 25° C. to 99° C. were used to calculate the thermal denaturation temperature ($T_m$). The emission profiles and calculated denaturation temperature ($T_m$) for both proteins are shown in FIG. 3A. Both proteins exhibited a similar emission profile and $T_m$, TcdB2 at 50.1±0.6° C. and TcdB2$_{\Delta1769\text{-}1787}$ at 50.9±0.7° C. Thus, deletion of this region did not alter the thermal stability of TcdB2$_{\Delta1769\text{-}1787}$.

TcdB2$_{\Delta1769\text{-}1787}$ autoprocessing in the absence of exogenous IP6. Following expression and purification of TcdB2$_{\Delta1769\text{-}1787}$, we detected two proteins by SDS-PAGE, one of which appeared to be an autoprocessed form of the full-length mutant. Despite the fact that approximately 50% of the mutant appeared as an unprocessed band on SDS-PAGE (FIGS. 1B, 3C), cytotoxicity remained undetectable even at concentrations as high as 1 μM (data not shown), suggesting even the unprocessed fraction of $TcdB2_{\Delta1769\text{-}1787}$ lacked cytotoxic activity. In light of this, considered whether the apparent autoprocessing in the mutant was due to endogenous APD activity, and whether the unprocessed portion of $TcdB2_{\Delta1769\text{-}1787}$ was capable of IP6 induced autoprocessing.

C698 in $TcdB2_{\Delta1769\text{-}1787}$ was converted to S698, a mutation previously shown to prevent the autoproteolytic cleavage event from occurring even in the presence of IP6. As shown in FIG. 3E, when cysteine protease activity was repressed by mutating C698, $TcdB2_{\Delta1769\text{-}1787:C698S}$ no longer appeared to spontaneously autoprocess, and ran as a single 270 kDa band on SDS-PAGE. We next examined the cytotoxicity of $TcdB2_{\Delta1769\text{-}1787:C698S}$ on CHO-K1 cells, and found that preventing autoprocessing with this mutation was not sufficient to restore cytotoxicity (FIG. 3F).

Then we took advantage of the fact that the protein is purified using a carboxy-terminal his-tag. Consequently, the amino-terminal autoprocessed fragment of $TcdB2_{\Delta1769\text{-}1787}$, comprised of the GTD ($TcdB_{1\text{-}543}$), is eliminated during purification as it lacks the his-tag and thus will not bind the affinity column. In the mutant, the purification process then results in isolation of only the full-length mutant and the larger autoprocessing cleavage product. By using an antibody which recognizes the amino-terminal region of TcdB, we were able to assess whether autoprocessing occurred after the addition of IP6 in both TcdB2 and $TcdB2_{\Delta1769\text{-}1787}$. As shown in the immunoblot in FIG. 3B, incubating $TcdB2_{\Delta1769\text{-}1787}$ with IP6 results in additional autoprocessing of the mutant, evidenced by the appearance of the smaller 60 kDa fragment in these samples. Moreover, this appears to occur at a level similar to that observed in full-length TcdB2 (FIGS. 3B-D).

$TcdB2_{\Delta1769\text{-}1787}$ exhibits reduced cell association in comparison to TcdB2. Previous work has indicated amino acids 1756-1780 are necessary for translocation of TcdB1 across the endocytic vesicle membrane. As we did not observe a return of cytotoxicity when autoprocessing was precluded in $TcdB2_{\Delta1769\text{-}1787:C698S}$ we considered that a deletion of residues 1769-1787 would have similar effects on the translocation of TcdB2. To first determine if $TcdB2_{\Delta1769\text{-}1787}$ associated with cells to the same extent as TcdB2, each protein was applied to both CHO-K1 and HeLa cells. Total cell extracts were then collected and subjected to immunoblot analysis using antibody against the amino-terminal region of TcdB. Recognizing that spontaneous autoprocessing could reduce the total amount of protein capable of interacting with cells, $TcdB2_{\Delta1769\text{-}1787:C698S}$ as well as $TcdB2_{C698S}$ were also assessed for interaction with cells. Counter to our prediction that $TcdB2_{\Delta1769\text{-}1787}$ would be unable to translocate across the vesicle membrane, no detectable mutant protein interaction was found with these cells, as seen in FIGS. 4A and 4B. Thus $TcdB2_{\Delta1769\text{-}1787}$ appears to be unable to bind cells. In contrast, both TcdB2 and $TcdB2_{C698S}$ interacted with cells (FIGS. 4A and 4B). The lack of detectable cell interactions by $TcdB2_{\Delta1769\text{-}1787}$ and $TcdB2_{\Delta1769\text{-}1787:C698S}$ suggested the lack of cell binding in $TcdB2_{\Delta1769\text{-}1787}$ was not solely due to spontaneous autoprocessing. While this immunoblot method does not distinguish between surface bound and internalized toxin, collectively, the data shown indicates $TcdB2_{\Delta1769\text{-}1787}$ is unable to associate with target cells at a level similar to that of TcdB2.

Though both TcdB2 and $TcdB2_{\Delta1769\text{-}1787}$ appear to be equally detected by the anti-TcdB antibody (FIG. 3B), we recognized it was possible that the $TcdB2_{\Delta1769\text{-}1787}$ mutant bound the cell but was rapidly degraded or the antibody-binding region was altered during interaction with the cell. As a second approach to measure cell interaction, $TcdB2_{\Delta1769\text{-}1787}$ and TcdB2 were labeled with Alexa-fluor488 and incubated with CHO cells for 30 min before being examined by fluorescent microscopy. Labeled TcdB2 yielded a pronounced signal on treated cells, while $TcdB2_{\Delta1769\text{-}1787}$ interaction was below the level of detection (FIG. 4C).

$TcdB2_{\Delta1769\text{-}1787}$ induces a neutralizing antibody response that correlates with protection from CDI in a murine model. Whether $TcdB2_{\Delta1769\text{-}1787}$ was able to induce an antibody response capable of neutralizing TcdB2 and protecting against CDI was investigated, and whether this response was similar in effectiveness to that generated against a glucosyltransferase defective form of TcdB2, used as a full-length control.

Mice were vaccinated with $TcdB2_{\Delta1769\text{-}1787}$ or $TcdB2_{D270N}$ (a variant defective in glucosyltransferase activity) and then boosted at 28 days, as outlined in the schematic (FIG. 5A). Two weeks following the booster vaccination, the animals began antibiotic treatment to predispose them to *C. difficile* infection. Mice were orally gavaged with *C. difficile* spores to establish infection, and then weighed daily for two weeks. Animals vaccinated with $TcdB2_{\Delta1769\text{-}1787}$ or $TcdB2_{D270N}$ experienced significantly less weight loss than the non-immunized mice, with their weight loss stabilizing within 48 h (FIG. 5B). The total *C. difficile CFUs were measured across groups at days* 0, 2, 4, 7, and 10 post-infection, yet there were no significant differences detected between groups (FIG. 5C). These findings indicated that the vaccinated animals are able to effectively neutralize TcdB, therefore protecting them from the weight loss associated with disease, despite the animals carrying the same burden of *C. difficile* across infection time-points. To specifically test whether or not vaccinated animals produced antibodies capable of neutralizing TcdB2, CHO-K1 cells were treated with TcdB2, either with or without a 1:100 dilution of sera from vaccinated animals and non-immunized controls. Sera from days 14 and 28 showed no effect on cell viability across all groups. Cells treated with day 42 and post-CDI sera from $TcdB2_{\Delta1769\text{-}1787}$—vaccinated animals showed significantly increased cell viability compared with cells treated with toxin alone.

Endpoint TcdB2-specific antibody titers were determined by ELISA at days 14, 28, 42, and post-CDI. Animals vaccinated with $TcdB2_{\Delta1769\text{-}1787}$ showed significantly higher TcdB2 specific IgG1 titers at days 14 ($p<0.05$), 28 ($p<0.05$), 42 ($p<0.001$) and following CDI ($p<0.001$) when compared with non-immunized controls. These data show $TcdB2_{\Delta1769\text{-}1787}$ is capable of stimulating an immune response in the murine model, and that this response correlates with protection against disease as measured by weight loss.

The results of the example indicate that amino acids 1769-1787 have an influence on the conformation of TcdB2. The deletion of this region in TcdB2 led to spontaneous autoprocessing, and to a reduction in cell binding. Unexpectedly, this mutant protein exhibited a greater than 10,000-fold reduction in cytotoxicity despite retaining enzymatic activities in vitro. The deletion mutant was still able to undergo IP6-induced autoprocessing at a similar level to that seen in full-length TcdB2. Finally, we found $TcdB2_{\Delta1769\text{-}1787}$ retains important epitope profiles and induces a strong neutralizing antibody response sufficient to reduce the severity of C. difficile infection in a mouse model. As noted, TcdB2$_{\Delta1769\text{-}1787}$ does not exhibit detectable cytotoxicity. As part of the vaccination protocol mice were administered 50 µg of protein, which is 2000 times the calculated LD$_{50}$ of TcdB2, and no detrimental effects were observed.

In at least certain embodiments, the present disclosure is directed to a deletion mutant of a Clostridioides difficile TcdB toxin, comprising a deletion of 19 amino acids corresponding to amino acids 1769 to 1787 of the TcdB toxin, the deletion mutant having immunogenic activity. The TcdB toxin may have amino acid sequence SEQ ID NO:1 or SEQ ID NO:3, or may have an amino acid sequence having at least 90% identity to SEQ ID NO:1 or SEQ ID NO:3. The TcdB toxin may be a TcdB2 toxin from a C. difficile strain selected from the group consisting of strains BI17, NAP1, B1, 027, and R20291. The TcdB toxin may be a TcdB1 toxin from a C. difficile strain VPI 10463. The deletion mutant may comprise at least one amino acid substitution or deletion in a region of the TcdB toxin corresponding to amino acids 1753-1768 and/or amino acids 1788-1852. The deletion mutant may be expressed from a recombinant source. The deletion mutant may be absent a contiguous sequence of amino acids comprising NVFKGNTISDKISFNFSDK (SEQ ID NO:2) or NVFKDKTLANKLSFNFSDK (SEQ ID NO:4).

In at least certain embodiments, the present disclosure is directed to a vaccine composition comprising any one or more of the deletion mutants described above, the composition further comprising a pharmaceutically-acceptable excipient. The vaccine composition may further comprise an adjuvant. In at least certain embodiments, the present disclosure is directed to a method of stimulating an immune response in a subject against Clostridioides difficile, comprising administering to the subject the vaccine composition described above in an amount sufficient to induce an immunogenic response in the subject. The vaccine composition may comprise an adjuvant. The subject may be a patient in a population at elevated risk for incurring a C. difficile infection, the population comprising workers and patients in healthcare, nursing home, assisted-living, or retirement facilities, candidates for surgical procedures, recipients of extended antibiotic or steroid treatment, patients having celiac disease, autoimmune diseases, AIDS, and/or inflammatory bowel disease, or who are immunosuppressed.

The treatment may be provided to the subject prior to a surgery, immunotherapy, antibiotic therapy, or C. difficile treatment performed on the subject. In at least certain embodiments, the present disclosure is directed to a nucleic acid comprising a nucleic acid sequence which encodes a deletion mutant as described above. In at least certain embodiments, the present disclosure is directed to a vector, comprising said nucleic acid. In at least certain embodiments, the present disclosure is directed to a host cell comprising said vector.

While the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the inventive concepts of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure. Changes may be made in the formulation of the various compositions described herein, the methods described herein or in the steps or the sequence of steps of the methods described herein without departing from the spirit and scope of the present disclosure. Further, while various embodiments of the present disclosure have been described in particular claims herein below, it is not intended that the present disclosure be limited to these particular claims.

What is claimed is:

1. A deletion mutant of a Clostridioides *difficile* TcdB toxin, comprising:
   at least one deletion consisting of amino acids 1769 to 1787 of the TedB toxin, the deletion mutant having immunogenic activity, wherein the TedB toxin has an amino acid sequence selected from the group consisting of SEQ ID NO: 1 and SEQ ID NO:3; and wherein the deletion mutant has at least 90% identity to the TcdB toxin.

2. The deletion mutant of claim 1 having at least 95% identity to the TedB toxin.

3. The deletion mutant of claim 1, wherein the TedB toxin is a TcdB2 toxin from a *C. difficile* strain selected from the group consisting of strains BI17, NAP1, B1, 027, and R20291.

4. The deletion mutant of claim 1, wherein the TedB toxin is a TedB1 toxin from a *C. difficile* strain VPI 10463.

5. The deletion mutant of claim 1, further comprising at least one amino acid substitution or deletion in a region corresponding to amino acids 1-1752, 1753-1768 and/or amino acids 1788-1852 of the TedB toxin.

6. The deletion mutant of claim 1, wherein the deletion mutant is expressed from a recombinant source.

7. A vaccine composition comprising the deletion mutant of claim 1, and a pharmaceutically-acceptable excipient.

8. The vaccine composition of claim 7, further comprising an adjuvant.

9. A method of stimulating an immune response in a subject against Clostridioides *difficile*, comprising administering to the subject an amount of the vaccine composition of claim 7 sufficient to induce an immunogenic response in the subject.

10. The method of claim 9, wherein the vaccine composition comprises an adjuvant.

11. The method of claim 9, wherein the subject is a patient in a population at elevated risk for incurring a *C. difficile* infection, the population comprising workers and patients in healthcare, nursing home, assisted-living, or retirement facilities, candidates for surgical procedures, recipients of extended antibiotic or steroid treatment, patients having celiac disease, autoimmune diseases, AIDS, and/or inflammatory bowel disease, or who are immunesuppressed.

12. The method of claim 9, wherein the treatment is provided to the subject prior to a surgery, immunotherapy, antibiotic therapy, or *C. difficile* treatment performed on the subject.

13. A nucleic acid, comprising a nucleic acid sequence which encodes the deletion mutant of claim 1.

14. A vector, comprising the nucleic acid of claim 13.

15. A host cell, comprising the vector of claim 14.

* * * * *

SEQUENCE LISTING

```
<160> NUMBER OF SEQ ID NOS: 4

<210> SEQ ID NO 1
<211> LENGTH: 2366
<212> TYPE: PRT
<213> ORGANISM: Clostridium difficile

<400> SEQUENCE: 1

Met Ser Leu Val Asn Arg Lys Gln Leu Glu Lys Met Ala Asn Val Arg
1               5                   10                  15

Phe Arg Val Gln Glu Asp Glu Tyr Val Ala Ile Leu Asp Ala Leu Glu
                20                  25                  30

Glu Tyr His Asn Met Ser Glu Asn Thr Val Val Glu Lys Tyr Leu Lys
            35                  40                  45

Leu Lys Asp Ile Asn Ser Leu Thr Asp Ile Tyr Ile Asp Thr Tyr Lys
        50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
```

-continued

```
                100                 105                 110
Asn Tyr Ile Asn Gln Trp Lys Asp Val Asn Ser Asp Tyr Asn Val Asn
            115                 120                 125
Val Phe Tyr Asp Ser Asn Ala Phe Leu Ile Asn Thr Leu Lys Lys Thr
        130                 135                 140
Ile Val Glu Ser Ala Thr Asn Asp Thr Leu Glu Ser Phe Arg Glu Asn
145                 150                 155                 160
Leu Asn Asp Pro Arg Phe Asp Tyr Asn Lys Phe Tyr Arg Lys Arg Met
                165                 170                 175
Glu Ile Ile Tyr Asp Lys Gln Lys Asn Phe Ile Asn Tyr Tyr Lys Thr
            180                 185                 190
Gln Arg Glu Glu Asn Pro Asp Leu Ile Ile Asp Asp Ile Val Lys Ile
        195                 200                 205
Tyr Leu Ser Asn Glu Tyr Ser Lys Asp Ile Asp Glu Leu Asn Ser Tyr
    210                 215                 220
Ile Glu Glu Ser Leu Asn Lys Val Thr Glu Asn Ser Gly Asn Asp Val
225                 230                 235                 240
Arg Asn Phe Glu Glu Phe Lys Gly Gly Glu Ser Phe Lys Leu Tyr Glu
                245                 250                 255
Gln Glu Leu Val Glu Arg Trp Asn Leu Ala Ala Ala Ser Asp Ile Leu
            260                 265                 270
Arg Ile Ser Ala Leu Lys Glu Val Gly Val Tyr Leu Asp Val Asp
        275                 280                 285
Met Leu Pro Gly Ile Gln Pro Asp Leu Phe Glu Ser Ile Glu Lys Pro
    290                 295                 300
Ser Ser Val Thr Val Asp Phe Trp Glu Met Val Lys Leu Glu Ala Ile
305                 310                 315                 320
Met Lys Tyr Lys Glu Tyr Ile Pro Gly Tyr Thr Ser Glu His Phe Asp
                325                 330                 335
Met Leu Asp Glu Glu Val Gln Ser Ser Phe Glu Ser Val Leu Ala Ser
            340                 345                 350
Lys Ser Asp Lys Ser Glu Ile Phe Ser Ser Leu Gly Asp Met Glu Ala
        355                 360                 365
Ser Pro Leu Glu Val Lys Ile Ala Phe Asn Ser Lys Gly Ile Ile Asn
    370                 375                 380
Gln Gly Leu Ile Ser Val Lys Asp Ser Tyr Cys Ser Asn Leu Ile Val
385                 390                 395                 400
Lys Gln Ile Glu Asn Arg Tyr Lys Ile Leu Asn Asn Ser Leu Asn Pro
                405                 410                 415
Ala Ile Ser Glu Asp Asn Asp Phe Asn Thr Thr Thr Asn Ala Phe Ile
            420                 425                 430
Asp Ser Ile Met Ala Glu Ala Asn Ala Asp Asn Gly Arg Phe Met Met
        435                 440                 445
Glu Leu Gly Lys Tyr Leu Arg Val Gly Phe Phe Pro Asp Val Lys Thr
    450                 455                 460
Thr Ile Asn Leu Ser Gly Pro Glu Ala Tyr Ala Ala Ala Tyr Gln Asp
465                 470                 475                 480
Leu Leu Met Phe Lys Glu Gly Ser Met Asn Ile His Leu Ile Glu Ala
                485                 490                 495
Asp Leu Arg Asn Phe Glu Ile Ser Lys Thr Asn Ile Ser Gln Ser Thr
            500                 505                 510
Glu Gln Glu Met Ala Ser Leu Trp Ser Phe Asp Asp Ala Arg Ala Lys
        515                 520                 525
```

```
Ala Gln Phe Glu Glu Tyr Lys Lys Asn Tyr Phe Gly Ser Leu Gly
    530                 535                 540
Glu Asp Asp Asn Leu Asp Phe Ser Gln Asn Thr Val Val Asp Lys Glu
545                 550                 555                 560
Tyr Leu Leu Glu Lys Ile Ser Ser Leu Ala Arg Ser Ser Glu Arg Gly
                565                 570                 575
Tyr Ile His Tyr Ile Val Gln Leu Gln Gly Asp Lys Ile Ser Tyr Glu
            580                 585                 590
Ala Ala Cys Asn Leu Phe Ala Lys Thr Pro Tyr Asp Ser Val Leu Phe
            595                 600                 605
Gln Lys Asn Ile Glu Asp Ser Glu Ile Ala Tyr Tyr Asn Pro Gly
    610                 615                 620
Asp Gly Glu Ile Gln Glu Ile Asp Lys Tyr Lys Ile Pro Ser Ile Ile
625                 630                 635                 640
Ser Asp Arg Pro Lys Ile Lys Leu Thr Phe Ile Gly His Gly Lys Asp
                645                 650                 655
Glu Phe Asn Thr Asp Ile Phe Ala Gly Leu Asp Val Asp Ser Leu Ser
            660                 665                 670
Thr Glu Ile Glu Thr Ala Ile Asp Leu Ala Lys Glu Asp Ile Ser Pro
            675                 680                 685
Lys Ser Ile Glu Ile Asn Leu Leu Gly Cys Asn Met Phe Ser Tyr Ser
    690                 695                 700
Val Asn Val Glu Glu Thr Tyr Pro Gly Lys Leu Leu Leu Arg Val Lys
705                 710                 715                 720
Asp Lys Val Ser Glu Leu Met Pro Ser Ile Ser Gln Asp Ser Ile Ile
                725                 730                 735
Val Ser Ala Asn Gln Tyr Glu Val Arg Ile Asn Ser Glu Gly Arg Arg
            740                 745                 750
Glu Leu Leu Asp His Ser Gly Glu Trp Ile Asn Lys Glu Glu Ser Ile
            755                 760                 765
Ile Lys Asp Ile Ser Ser Lys Glu Tyr Ile Ser Phe Asn Pro Lys Glu
    770                 775                 780
Asn Lys Ile Ile Val Lys Ser Lys Asn Leu Pro Glu Leu Ser Thr Leu
785                 790                 795                 800
Leu Gln Glu Ile Arg Asn Asn Ser Asn Ser Ser Asp Ile Glu Leu Glu
                805                 810                 815
Glu Lys Val Met Leu Ala Glu Cys Glu Ile Asn Val Ile Ser Asn Ile
            820                 825                 830
Asp Thr Gln Val Val Glu Gly Arg Ile Glu Glu Ala Lys Ser Leu Thr
            835                 840                 845
Ser Asp Ser Ile Asn Tyr Ile Lys Asn Glu Phe Lys Leu Ile Glu Ser
    850                 855                 860
Ile Ser Asp Ala Leu Tyr Asp Leu Lys Gln Gln Asn Glu Leu Glu Glu
865                 870                 875                 880
Ser His Phe Ile Ser Phe Glu Asp Ile Leu Glu Thr Asp Glu Gly Phe
                885                 890                 895
Ser Ile Arg Phe Ile Asp Lys Glu Thr Gly Glu Ser Ile Phe Val Glu
            900                 905                 910
Thr Glu Lys Ala Ile Phe Ser Glu Tyr Ala Asn His Ile Thr Glu Glu
            915                 920                 925
Ile Ser Lys Ile Lys Gly Thr Ile Phe Asp Thr Val Asn Gly Lys Leu
    930                 935                 940
```

-continued

```
Val Lys Lys Val Asn Leu Asp Ala Thr His Glu Val Asn Thr Leu Asn
945                 950                 955                 960

Ala Ala Phe Phe Ile Gln Ser Leu Ile Glu Tyr Asn Ser Ser Lys Glu
            965                 970                 975

Ser Leu Ser Asn Leu Ser Val Ala Met Lys Val Gln Val Tyr Ala Gln
            980                 985                 990

Leu Phe Ser Thr Gly Leu Asn Thr Ile Thr Asp Ala Ala Lys Val Val
        995                 1000                1005

Glu Leu Val Ser Thr Ala Leu Asp Glu Thr Ile Asp Leu Leu Pro
    1010                1015                1020

Thr Leu Ser Glu Gly Leu Pro Val Ile Ala Thr Ile Ile Asp Gly
    1025                1030                1035

Val Ser Leu Gly Ala Ala Ile Lys Glu Leu Ser Glu Thr Ser Asp
    1040                1045                1050

Pro Leu Leu Arg Gln Glu Ile Glu Ala Lys Ile Gly Ile Met Ala
    1055                1060                1065

Val Asn Leu Thr Ala Ala Thr Thr Ala Ile Ile Thr Ser Ser Leu
    1070                1075                1080

Gly Ile Ala Ser Gly Phe Ser Ile Leu Leu Val Pro Leu Ala Gly
    1085                1090                1095

Ile Ser Ala Gly Ile Pro Ser Leu Val Asn Asn Glu Leu Ile Leu
    1100                1105                1110

Arg Asp Lys Ala Thr Lys Val Val Asp Tyr Phe Ser His Ile Ser
    1115                1120                1125

Leu Ala Glu Ser Glu Gly Ala Phe Thr Ser Leu Asp Asp Lys Ile
    1130                1135                1140

Met Met Pro Gln Asp Asp Leu Val Ile Ser Glu Ile Asp Phe Asn
    1145                1150                1155

Asn Asn Ser Ile Thr Leu Gly Lys Cys Glu Ile Trp Arg Met Glu
    1160                1165                1170

Gly Gly Ser Gly His Thr Val Thr Asp Asp Ile Asp His Phe Phe
    1175                1180                1185

Ser Ala Pro Ser Ile Thr Tyr Arg Glu Pro His Leu Ser Ile Tyr
    1190                1195                1200

Asp Val Leu Glu Val Gln Lys Glu Glu Leu Asp Leu Ser Lys Asp
    1205                1210                1215

Leu Met Val Leu Pro Asn Ala Pro Asn Arg Val Phe Ala Trp Glu
    1220                1225                1230

Thr Gly Trp Thr Pro Gly Leu Arg Ser Leu Glu Asn Asp Gly Thr
    1235                1240                1245

Lys Leu Leu Asp Arg Ile Arg Asp Asn Tyr Glu Gly Glu Phe Tyr
    1250                1255                1260

Trp Arg Tyr Phe Ala Phe Ile Ala Asp Ala Leu Ile Thr Thr Leu
    1265                1270                1275

Lys Pro Arg Tyr Glu Asp Thr Asn Ile Arg Ile Asn Leu Asp Ser
    1280                1285                1290

Asn Thr Arg Ser Phe Ile Val Pro Val Ile Thr Thr Glu Tyr Ile
    1295                1300                1305

Arg Glu Lys Leu Ser Tyr Ser Phe Tyr Gly Ser Gly Gly Thr Tyr
    1310                1315                1320

Ala Leu Ser Leu Ser Gln Tyr Asn Met Asn Ile Asn Ile Glu Leu
    1325                1330                1335

Asn Glu Asn Asp Thr Trp Val Ile Asp Val Asp Asn Val Val Arg
```

```
                1340                1345                1350

Asp Val Thr Ile Glu Ser Asp Lys Ile Lys Gly Asp Leu Ile
    1355                1360                1365

Glu Asn Ile Leu Ser Lys Leu Ser Ile Glu Asp Asn Lys Ile Ile
    1370                1375                1380

Leu Asp Asn His Glu Ile Asn Phe Ser Gly Thr Leu Asn Gly Gly
    1385                1390                1395

Asn Gly Phe Val Ser Leu Thr Phe Ser Ile Leu Glu Gly Ile Asn
    1400                1405                1410

Ala Val Ile Glu Val Asp Leu Leu Ser Lys Ser Tyr Lys Val Leu
    1415                1420                1425

Ile Ser Gly Glu Leu Lys Thr Leu Met Ala Asn Ser Asn Ser Val
    1430                1435                1440

Gln Gln Lys Ile Asp Tyr Ile Gly Leu Asn Ser Glu Leu Gln Lys
    1445                1450                1455

Asn Ile Pro Tyr Ser Phe Met Asp Asp Lys Gly Lys Glu Asn Gly
    1460                1465                1470

Phe Ile Asn Cys Ser Thr Lys Glu Gly Leu Phe Val Ser Glu Leu
    1475                1480                1485

Ser Asp Val Val Leu Ile Ser Lys Val Tyr Met Asp Asn Ser Lys
    1490                1495                1500

Pro Leu Phe Gly Tyr Cys Ser Asn Asp Leu Lys Asp Val Lys Val
    1505                1510                1515

Ile Thr Lys Asp Asp Val Ile Ile Leu Thr Gly Tyr Tyr Leu Lys
    1520                1525                1530

Asp Asp Ile Lys Ile Ser Leu Ser Phe Thr Ile Gln Asp Glu Asn
    1535                1540                1545

Thr Ile Lys Leu Asn Gly Val Tyr Leu Asp Glu Asn Gly Val Ala
    1550                1555                1560

Glu Ile Leu Lys Phe Met Asn Lys Lys Gly Ser Thr Asn Thr Ser
    1565                1570                1575

Asp Ser Leu Met Ser Phe Leu Glu Ser Met Asn Ile Lys Ser Ile
    1580                1585                1590

Phe Ile Asn Ser Leu Gln Ser Asn Thr Lys Leu Ile Leu Asp Thr
    1595                1600                1605

Asn Phe Ile Ile Ser Gly Thr Thr Ser Ile Gly Gln Phe Glu Phe
    1610                1615                1620

Ile Cys Asp Lys Asp Asn Asn Ile Gln Pro Tyr Phe Ile Lys Phe
    1625                1630                1635

Asn Thr Leu Glu Thr Lys Tyr Thr Leu Tyr Val Gly Asn Arg Gln
    1640                1645                1650

Asn Met Ile Val Glu Pro Asn Tyr Asp Leu Asp Asp Ser Gly Asp
    1655                1660                1665

Ile Ser Ser Thr Val Ile Asn Phe Ser Gln Lys Tyr Leu Tyr Gly
    1670                1675                1680

Ile Asp Ser Cys Val Asn Lys Val Ile Ile Ser Pro Asn Ile Tyr
    1685                1690                1695

Thr Asp Glu Ile Asn Ile Thr Pro Ile Tyr Glu Ala Asn Asn Thr
    1700                1705                1710

Tyr Pro Glu Val Ile Val Leu Asp Thr Asn Tyr Ile Ser Glu Lys
    1715                1720                1725

Ile Asn Ile Asn Ile Asn Asp Leu Ser Ile Arg Tyr Val Trp Ser
    1730                1735                1740
```

```
Asn Asp Gly Ser Asp Phe Ile Leu Met Ser Thr Asp Glu Glu Asn
    1745             1750                 1755

Lys Val Ser Gln Val Lys Ile Arg Phe Thr Asn Val Phe Lys Gly
1760             1765                 1770

Asn Thr Ile Ser Asp Lys Ile Ser Phe Asn Phe Ser Asp Lys Gln
    1775             1780                 1785

Asp Val Ser Ile Asn Lys Val Ile Ser Thr Phe Thr Pro Ser Tyr
    1790             1795                 1800

Tyr Val Glu Gly Leu Leu Asn Tyr Asp Leu Gly Leu Ile Ser Leu
    1805             1810                 1815

Tyr Asn Glu Lys Phe Tyr Ile Asn Asn Phe Gly Met Met Val Ser
    1820             1825                 1830

Gly Leu Val Tyr Ile Asn Asp Ser Leu Tyr Tyr Phe Lys Pro Pro
    1835             1840                 1845

Ile Lys Asn Leu Ile Thr Gly Phe Thr Thr Ile Gly Asp Asp Lys
1850             1855                 1860

Tyr Tyr Phe Asn Pro Asp Asn Gly Gly Ala Ala Ser Val Gly Glu
    1865             1870                 1875

Thr Ile Ile Asp Gly Lys Asn Tyr Tyr Phe Ser Gln Asn Gly Val
    1880             1885                 1890

Leu Gln Thr Gly Val Phe Ser Thr Glu Asp Gly Phe Lys Tyr Phe
    1895             1900                 1905

Ala Pro Ala Asp Thr Leu Asp Glu Asn Leu Glu Gly Glu Ala Ile
    1910             1915                 1920

Asp Phe Thr Gly Lys Leu Thr Ile Asp Glu Asn Val Tyr Tyr Phe
    1925             1930                 1935

Gly Asp Asn Tyr Arg Ala Ala Ile Glu Trp Gln Thr Leu Asp Asp
    1940             1945                 1950

Glu Val Tyr Tyr Phe Ser Asp Thr Gly Arg Ala Phe Lys Gly
    1955             1960                 1965

Leu Asn Gln Ile Gly Asp Asp Lys Phe Tyr Phe Asn Ser Asp Gly
    1970             1975                 1980

Ile Met Gln Lys Gly Phe Val Asn Ile Asn Asp Lys Thr Phe Tyr
    1985             1990                 1995

Phe Asp Asp Ser Gly Val Met Lys Ser Gly Tyr Thr Glu Ile Asp
    2000             2005                 2010

Gly Lys Tyr Phe Tyr Phe Ala Glu Asn Gly Glu Met Gln Ile Gly
    2015             2020                 2025

Val Phe Asn Thr Ala Asp Gly Phe Lys Tyr Phe Ala His His Asp
    2030             2035                 2040

Glu Asp Leu Gly Asn Glu Glu Gly Glu Ala Leu Ser Tyr Ser Gly
    2045             2050                 2055

Ile Leu Asn Phe Asn Asn Lys Ile Tyr Tyr Phe Asp Asp Ser Phe
    2060             2065                 2070

Thr Ala Val Val Gly Trp Lys Asp Leu Glu Asp Gly Ser Lys Tyr
    2075             2080                 2085

Tyr Phe Asp Glu Asp Thr Ala Glu Ala Tyr Ile Gly Ile Ser Ile
    2090             2095                 2100

Ile Asn Asp Gly Lys Tyr Tyr Phe Asn Asp Ser Gly Ile Met Gln
    2105             2110                 2115

Ile Gly Phe Val Thr Ile Asn Asn Glu Val Phe Tyr Phe Ser Asp
    2120             2125                 2130
```

-continued

```
Ser Gly Ile Val Glu Ser Gly Met Gln Asn Ile Asp Asp Asn Tyr
    2135                2140                2145

Phe Tyr Ile Asp Glu Asn Gly Leu Val Gln Ile Gly Val Phe Asp
    2150                2155                2160

Thr Ser Asp Gly Tyr Lys Tyr Phe Ala Pro Ala Asn Thr Val Asn
    2165                2170                2175

Asp Asn Ile Tyr Gly Gln Ala Val Glu Tyr Ser Gly Leu Val Arg
    2180                2185                2190

Val Gly Glu Asp Val Tyr Tyr Phe Gly Glu Thr Tyr Thr Ile Glu
    2195                2200                2205

Thr Gly Trp Ile Tyr Asp Met Glu Asn Glu Ser Asp Lys Tyr Tyr
    2210                2215                2220

Phe Asp Pro Glu Thr Lys Lys Ala Tyr Lys Gly Ile Asn Val Ile
    2225                2230                2235

Asp Asp Ile Lys Tyr Tyr Phe Asp Glu Asn Gly Ile Met Arg Thr
    2240                2245                2250

Gly Leu Ile Thr Phe Glu Asp Asn His Tyr Tyr Phe Asn Glu Asp
    2255                2260                2265

Gly Ile Met Gln Tyr Gly Tyr Leu Asn Ile Glu Asp Lys Thr Phe
    2270                2275                2280

Tyr Phe Ser Glu Asp Gly Ile Met Gln Ile Gly Val Phe Asn Thr
    2285                2290                2295

Pro Asp Gly Phe Lys Tyr Phe Ala His Gln Asn Thr Leu Asp Glu
    2300                2305                2310

Asn Phe Glu Gly Glu Ser Ile Asn Tyr Thr Gly Trp Leu Asp Leu
    2315                2320                2325

Asp Glu Lys Arg Tyr Tyr Phe Thr Asp Glu Tyr Ile Ala Ala Thr
    2330                2335                2340

Gly Ser Val Ile Ile Asp Gly Glu Glu Tyr Tyr Phe Asp Pro Asp
    2345                2350                2355

Thr Ala Gln Leu Val Ile Ser Glu
    2360                2365

<210> SEQ ID NO 2
<211> LENGTH: 19
<212> TYPE: PRT
<213> ORGANISM: Artificial Sequence
<220> FEATURE:
<223> OTHER INFORMATION: TcdB2

<400> SEQUENCE: 2

Asn Val Phe Lys Gly Asn Thr Ile Ser Asp Lys Ile Ser Phe Asn Phe
1               5                   10                  15

Ser Asp Lys

<210> SEQ ID NO 3
<211> LENGTH: 2366
<212> TYPE: PRT
<213> ORGANISM: Clostridium difficile

<400> SEQUENCE: 3

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
                20                  25                  30

Glu Tyr His Asn Met Ser Glu Asn Thr Val Val Glu Lys Tyr Leu Lys
            35                  40                  45
```

```
Leu Lys Asp Ile Asn Ser Leu Thr Asp Ile Tyr Ile Asp Thr Tyr Lys
    50              55                  60
Lys Ser Gly Arg Asn Lys Ala Leu Lys Lys Phe Lys Glu Tyr Leu Val
65              70                  75                  80
Thr Glu Val Leu Glu Leu Lys Asn Asn Asn Leu Thr Pro Val Glu Lys
                    85                  90                  95
Asn Leu His Phe Val Trp Ile Gly Gly Gln Ile Asn Asp Thr Ala Ile
                100                 105                 110
Asn Tyr Ile Asn Gln Trp Lys Asp Val Asn Ser Asp Tyr Asn Val Asn
            115                 120                 125
Val Phe Tyr Asp Ser Asn Ala Phe Leu Ile Asn Thr Leu Lys Lys Thr
    130                 135                 140
Val Val Glu Ser Ala Ile Asn Asp Thr Leu Glu Ser Phe Arg Glu Asn
145                 150                 155                 160
Leu Asn Asp Pro Arg Phe Asp Tyr Asn Lys Phe Phe Arg Lys Arg Met
                165                 170                 175
Glu Ile Ile Tyr Asp Lys Gln Lys Asn Phe Ile Asn Tyr Tyr Lys Ala
                180                 185                 190
Gln Arg Glu Glu Asn Pro Glu Leu Ile Ile Asp Asp Ile Val Lys Thr
            195                 200                 205
Tyr Leu Ser Asn Glu Tyr Ser Lys Glu Ile Asp Glu Leu Asn Thr Tyr
    210                 215                 220
Ile Glu Glu Ser Leu Asn Lys Ile Thr Gln Asn Ser Gly Asn Asp Val
225                 230                 235                 240
Arg Asn Phe Glu Glu Phe Lys Asn Gly Glu Ser Phe Asn Leu Tyr Glu
                245                 250                 255
Gln Glu Leu Val Glu Arg Trp Asn Leu Ala Ala Ala Ser Asp Ile Leu
                260                 265                 270
Arg Ile Ser Ala Leu Lys Glu Ile Gly Gly Met Tyr Leu Asp Val Asp
            275                 280                 285
Met Leu Pro Gly Ile Gln Pro Asp Leu Phe Glu Ser Ile Glu Lys Pro
    290                 295                 300
Ser Ser Val Thr Val Asp Phe Trp Glu Met Thr Lys Leu Glu Ala Ile
305                 310                 315                 320
Met Lys Tyr Lys Glu Tyr Ile Pro Glu Tyr Thr Ser Glu His Phe Asp
                325                 330                 335
Met Leu Asp Glu Glu Val Gln Ser Ser Phe Glu Ser Val Leu Ala Ser
            340                 345                 350
Lys Ser Asp Lys Ser Glu Ile Phe Ser Ser Leu Gly Asp Met Glu Ala
            355                 360                 365
Ser Pro Leu Glu Val Lys Ile Ala Phe Asn Ser Lys Gly Ile Ile Asn
    370                 375                 380
Gln Gly Leu Ile Ser Val Lys Asp Ser Tyr Cys Ser Asn Leu Ile Val
385                 390                 395                 400
Lys Gln Ile Glu Asn Arg Tyr Lys Ile Leu Asn Asn Ser Leu Asn Pro
                405                 410                 415
Ala Ile Ser Glu Asp Asn Asp Phe Asn Thr Thr Thr Asn Thr Phe Ile
                420                 425                 430
Asp Ser Ile Met Ala Glu Ala Asn Ala Asp Asn Gly Arg Phe Met Met
            435                 440                 445
Glu Leu Gly Lys Tyr Leu Arg Val Gly Phe Phe Pro Asp Val Lys Thr
    450                 455                 460
```

```
Thr Ile Asn Leu Ser Gly Pro Glu Ala Tyr Ala Ala Tyr Gln Asp
465                 470                 475                 480

Leu Leu Met Phe Lys Glu Gly Ser Met Asn Ile His Leu Ile Glu Ala
            485                 490                 495

Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Asp Ala Arg Ala Lys
        515                 520                 525

Ala Gln Phe Glu Glu Tyr Lys Arg Asn Tyr Phe Gly Ser Leu Gly
    530                 535                 540

Glu Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
            580                 585                 590

Ala Ala Cys Asn Leu Phe Ala Lys Thr Pro Tyr Asp Ser Val Leu Phe
        595                 600                 605

Gln Lys Asn Ile Glu Asp Ser Glu Ile Ala Tyr Tyr Asn Pro Gly
    610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
            660                 665                 670

Thr Glu Ile Glu Ala Ala Ile Asp Leu Ala Lys Glu Asp Ile Ser Pro
        675                 680                 685

Lys Ser Ile Glu Ile Asn Leu Leu Gly Cys Asn Met Phe Ser Tyr Ser
        690                 695                 700

Ile Asn Val Glu Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
            725                 730                 735

Val Ser Ala Asn Gln Tyr Glu Val Arg Ile Asn Ser Glu Gly Arg Arg
        740                 745                 750

Glu Leu Leu Asp His Ser Gly Glu Trp Ile Asn Lys Glu Ser Ile
    755                 760                 765

Ile Lys Asp Ile Ser Ser Lys Val Tyr Ile Ser Phe Asn Pro Lys Glu
    770                 775                 780

Asn Lys Ile Thr Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
            805                 810                 815

Glu Lys Val Met Leu Thr Glu Cys Glu Ile Asn Val Ile Ser Asn Ile
        820                 825                 830

Asp Thr Gln Ile Val Glu Glu Arg Ile Glu Glu Ala Lys Asn Leu Thr
        835                 840                 845

Ser Asp Ser Ile Asn Tyr Ile Lys Asp Glu Phe Lys Leu Ile Glu Ser
        850                 855                 860

Ile Ser Asp Ala Leu Cys Asp Leu Lys Gln Gln Asn Glu Leu Glu Asp
865                 870                 875                 880

Ser His Phe Ile Ser Phe Glu Asp Ile Ser Glu Thr Asp Glu Gly Phe
```

-continued

```
                885                 890                 895
Ser Ile Arg Phe Ile Asn Lys Glu Thr Gly Glu Ser Ile Phe Val Glu
                    900                 905                 910

Thr Glu Lys Thr Ile Phe Ser Glu Tyr Ala Asn His Ile Thr Glu Glu
            915                 920                 925

Ile Ser Lys Ile Lys Gly Thr Ile Phe Asp Thr Val Asn Gly Lys Leu
        930                 935                 940

Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
                965                 970                 975

Ser Leu Ser Asn Leu Ser Val Ala Met Lys Val Gln Val Tyr Ala Gln
            980                 985                 990

Leu Phe Ser Thr Gly Leu Asn Thr Ile Thr Asp Ala Ala Lys Val Val
        995                 1000                1005

Glu Leu Val Ser Thr Ala Leu Asp Glu Thr Ile Asp Leu Leu Pro
    1010                1015                1020

Thr Leu Ser Glu Gly Leu Pro Ile Ile Ala Thr Ile Ile Asp Gly
    1025                1030                1035

Val Ser Leu Gly Ala Ala Ile Lys Glu Leu Ser Glu Thr Ser Asp
    1040                1045                1050

Pro Leu Leu Arg Gln Glu Ile Glu Ala Lys Ile Gly Ile Met Ala
    1055                1060                1065

Val Asn Leu Thr Thr Ala Thr Ala Ile Ile Thr Ser Ser Leu
    1070                1075                1080

Gly Ile Ala Ser Gly Phe Ser Ile Leu Leu Val Pro Leu Ala Gly
    1085                1090                1095

Ile Ser Ala Gly Ile Pro Ser Leu Val Asn Asn Glu Leu Val Leu
    1100                1105                1110

Arg Asp Lys Ala Thr Lys Val Val Asp Tyr Phe Lys His Val Ser
    1115                1120                1125

Leu Val Glu Thr Glu Gly Val Phe Thr Leu Leu Asp Asp Lys Ile
    1130                1135                1140

Met Met Pro Gln Asp Asp Leu Val Ile Ser Glu Ile Asp Phe Asn
    1145                1150                1155

Asn Asn Ser Ile Val Leu Gly Lys Cys Glu Ile Trp Arg Met Glu
    1160                1165                1170

Gly Gly Ser Gly His Thr Val Thr Asp Asp Ile Asp His Phe Phe
    1175                1180                1185

Ser Ala Pro Ser Ile Thr Tyr Arg Glu Pro His Leu Ser Ile Tyr
    1190                1195                1200

Asp Val Leu Glu Val Gln Lys Glu Glu Leu Asp Leu Ser Lys Asp
    1205                1210                1215

Leu Met Val Leu Pro Asn Ala Pro Asn Arg Val Phe Ala Trp Glu
    1220                1225                1230

Thr Gly Trp Thr Pro Gly Leu Arg Ser Leu Glu Asn Asp Gly Thr
    1235                1240                1245

Lys Leu Leu Asp Arg Ile Arg Asp Asn Tyr Glu Gly Glu Phe Tyr
    1250                1255                1260

Trp Arg Tyr Phe Ala Phe Ile Ala Asp Ala Leu Ile Thr Thr Leu
    1265                1270                1275

Lys Pro Arg Tyr Glu Asp Thr Asn Ile Arg Ile Asn Leu Asp Ser
    1280                1285                1290
```

```
Asn Thr Arg Ser Phe Ile Val Pro Ile Ile Thr Thr Glu Tyr Ile
1295                 1300                1305

Arg Glu Lys Leu Ser Tyr Ser Phe Tyr Gly Ser Gly Gly Thr Tyr
1310                 1315                1320

Ala Leu Ser Leu Ser Gln Tyr Asn Met Gly Ile Asn Ile Glu Leu
1325                 1330                1335

Ser Glu Ser Asp Val Trp Ile Ile Asp Val Asp Asn Val Val Arg
1340                 1345                1350

Asp Val Thr Ile Glu Ser Asp Lys Ile Lys Lys Gly Asp Leu Ile
1355                 1360                1365

Glu Gly Ile Leu Ser Thr Leu Ser Ile Glu Glu Asn Lys Ile Ile
1370                 1375                1380

Leu Asn Ser His Glu Ile Asn Phe Ser Gly Glu Val Asn Gly Ser
1385                 1390                1395

Asn Gly Phe Val Ser Leu Thr Phe Ser Ile Leu Glu Gly Ile Asn
1400                 1405                1410

Ala Ile Ile Glu Val Asp Leu Leu Ser Lys Ser Tyr Lys Leu Leu
1415                 1420                1425

Ile Ser Gly Glu Leu Lys Ile Leu Met Leu Asn Ser Asn His Ile
1430                 1435                1440

Gln Gln Lys Ile Asp Tyr Ile Gly Phe Asn Ser Glu Leu Gln Lys
1445                 1450                1455

Asn Ile Pro Tyr Ser Phe Val Asp Ser Glu Gly Lys Glu Asn Gly
1460                 1465                1470

Phe Ile Asn Gly Ser Thr Lys Glu Gly Leu Phe Val Ser Glu Leu
1475                 1480                1485

Pro Asp Val Val Leu Ile Ser Lys Val Tyr Met Asp Asp Ser Lys
1490                 1495                1500

Pro Ser Phe Gly Tyr Tyr Ser Asn Asn Leu Lys Asp Val Lys Val
1505                 1510                1515

Ile Thr Lys Asp Asn Val Asn Ile Leu Thr Gly Tyr Tyr Leu Lys
1520                 1525                1530

Asp Asp Ile Lys Ile Ser Leu Ser Leu Thr Leu Gln Asp Glu Lys
1535                 1540                1545

Thr Ile Lys Leu Asn Ser Val His Leu Asp Glu Ser Gly Val Ala
1550                 1555                1560

Glu Ile Leu Lys Phe Met Asn Arg Lys Gly Asn Thr Asn Thr Ser
1565                 1570                1575

Asp Ser Leu Met Ser Phe Leu Glu Ser Met Asn Ile Lys Ser Ile
1580                 1585                1590

Phe Val Asn Phe Leu Gln Ser Asn Ile Lys Phe Ile Leu Asp Ala
1595                 1600                1605

Asn Phe Ile Ile Ser Gly Thr Thr Ser Ile Gly Gln Phe Glu Phe
1610                 1615                1620

Ile Cys Asp Glu Asn Asp Asn Ile Gln Pro Tyr Phe Ile Lys Phe
1625                 1630                1635

Asn Thr Leu Glu Thr Asn Tyr Thr Leu Tyr Val Gly Asn Arg Gln
1640                 1645                1650

Asn Met Ile Val Glu Pro Asn Tyr Asp Leu Asp Asp Ser Gly Asp
1655                 1660                1665

Ile Ser Ser Thr Val Ile Asn Phe Ser Gln Lys Tyr Leu Tyr Gly
1670                 1675                1680
```

```
Ile Asp Ser Cys Val Asn Lys Val Val Ile Ser Pro Asn Ile Tyr
1685                1690                1695

Thr Asp Glu Ile Asn Ile Thr Pro Val Tyr Glu Thr Asn Asn Thr
1700                1705                1710

Tyr Pro Glu Val Ile Val Leu Asp Ala Asn Tyr Ile Asn Glu Lys
1715                1720                1725

Ile Asn Val Asn Ile Asn Asp Leu Ser Ile Arg Tyr Val Trp Ser
1730                1735                1740

Asn Asp Gly Asn Asp Phe Ile Leu Met Ser Thr Ser Glu Glu Asn
1745                1750                1755

Lys Val Ser Gln Val Lys Ile Arg Phe Val Asn Val Phe Lys Asp
1760                1765                1770

Lys Thr Leu Ala Asn Lys Leu Ser Phe Asn Phe Ser Asp Lys Gln
1775                1780                1785

Asp Val Pro Val Ser Glu Ile Ile Leu Ser Phe Thr Pro Ser Tyr
1790                1795                1800

Tyr Glu Asp Gly Leu Ile Gly Tyr Asp Leu Gly Leu Val Ser Leu
1805                1810                1815

Tyr Asn Glu Lys Phe Tyr Ile Asn Asn Phe Gly Met Met Val Ser
1820                1825                1830

Gly Leu Ile Tyr Ile Asn Asp Ser Leu Tyr Tyr Phe Lys Pro Pro
1835                1840                1845

Val Asn Asn Leu Ile Thr Gly Phe Val Thr Val Gly Asp Asp Lys
1850                1855                1860

Tyr Tyr Phe Asn Pro Ile Asn Gly Gly Ala Ala Ser Ile Gly Glu
1865                1870                1875

Thr Ile Ile Asp Asp Lys Asn Tyr Tyr Phe Asn Gln Ser Gly Val
1880                1885                1890

Leu Gln Thr Gly Val Phe Ser Thr Glu Asp Gly Phe Lys Tyr Phe
1895                1900                1905

Ala Pro Ala Asn Thr Leu Asp Glu Asn Leu Glu Gly Glu Ala Ile
1910                1915                1920

Asp Phe Thr Gly Lys Leu Ile Ile Asp Glu Asn Ile Tyr Tyr Phe
1925                1930                1935

Asp Asp Asn Tyr Arg Gly Ala Val Glu Trp Lys Glu Leu Asp Gly
1940                1945                1950

Glu Met His Tyr Phe Ser Pro Glu Thr Gly Lys Ala Phe Lys Gly
1955                1960                1965

Leu Asn Gln Ile Gly Asp Tyr Lys Tyr Tyr Phe Asn Ser Asp Gly
1970                1975                1980

Val Met Gln Lys Gly Phe Val Ser Ile Asn Asp Asn Lys His Tyr
1985                1990                1995

Phe Asp Asp Ser Gly Val Met Lys Val Gly Tyr Thr Glu Ile Asp
2000                2005                2010

Gly Lys His Phe Tyr Phe Ala Glu Asn Gly Glu Met Gln Ile Gly
2015                2020                2025

Val Phe Asn Thr Glu Asp Gly Phe Lys Tyr Phe Ala His His Asn
2030                2035                2040

Glu Asp Leu Gly Asn Glu Glu Gly Glu Glu Ile Ser Tyr Ser Gly
2045                2050                2055

Ile Leu Asn Phe Asn Asn Lys Ile Tyr Tyr Phe Asp Asp Ser Phe
2060                2065                2070

Thr Ala Val Val Gly Trp Lys Asp Leu Glu Asp Gly Ser Lys Tyr
```

```
                    2075                2080                2085

Tyr Phe Asp Glu Asp Thr Ala Glu Ala Tyr Ile Gly Leu Ser Leu
            2090                2095                2100

Ile Asn Asp Gly Gln Tyr Tyr Phe Asn Asp Gly Ile Met Gln
        2105                2110                2115

Val Gly Phe Val Thr Ile Asn Asp Lys Val Phe Tyr Phe Ser Asp
            2120                2125                2130

Ser Gly Ile Ile Glu Ser Gly Val Gln Asn Ile Asp Asp Asn Tyr
            2135                2140                2145

Phe Tyr Ile Asp Asp Asn Gly Ile Val Gln Ile Gly Val Phe Asp
            2150                2155                2160

Thr Ser Asp Gly Tyr Lys Tyr Phe Ala Pro Ala Asn Thr Val Asn
            2165                2170                2175

Asp Asn Ile Tyr Gly Gln Ala Val Glu Tyr Ser Gly Leu Val Arg
            2180                2185                2190

Val Gly Glu Asp Val Tyr Tyr Phe Gly Glu Thr Tyr Thr Ile Glu
            2195                2200                2205

Thr Gly Trp Ile Tyr Asp Met Glu Asn Glu Ser Asp Lys Tyr Tyr
            2210                2215                2220

Phe Asn Pro Glu Thr Lys Lys Ala Cys Lys Gly Ile Asn Leu Ile
            2225                2230                2235

Asp Asp Ile Lys Tyr Tyr Phe Asp Glu Lys Gly Ile Met Arg Thr
            2240                2245                2250

Gly Leu Ile Ser Phe Glu Asn Asn Asn Tyr Tyr Phe Asn Glu Asn
            2255                2260                2265

Gly Glu Met Gln Phe Gly Tyr Ile Asn Ile Glu Asp Lys Met Phe
            2270                2275                2280

Tyr Phe Gly Glu Asp Gly Val Met Gln Ile Gly Val Phe Asn Thr
            2285                2290                2295

Pro Asp Gly Phe Lys Tyr Phe Ala His Gln Asn Thr Leu Asp Glu
            2300                2305                2310

Asn Phe Glu Gly Glu Ser Ile Asn Tyr Thr Gly Trp Leu Asp Leu
            2315                2320                2325

Asp Glu Lys Arg Tyr Tyr Phe Thr Asp Glu Tyr Ile Ala Ala Thr
            2330                2335                2340

Gly Ser Val Ile Ile Asp Gly Glu Glu Tyr Tyr Phe Asp Pro Asp
            2345                2350                2355

Thr Ala Gln Leu Val Ile Ser Glu
            2360                2365

<210> SEQ ID NO 4
<211> LENGTH: 19
<212> TYPE: PRT
<213> ORGANISM: Artificial Sequence
<220> FEATURE:
<223> OTHER INFORMATION: TcdB1

<400> SEQUENCE: 4

Asn Val Phe Lys Asp Lys Thr Leu Ala Asn Lys Leu Ser Phe Asn Phe
1               5                   10                  15

Ser Asp Lys
```